US008452259B2

(12) United States Patent
Ellis et al.

(10) Patent No.: US 8,452,259 B2
(45) Date of Patent: May 28, 2013

(54) MODULAR PERSONAL NETWORK SYSTEMS AND METHODS

(75) Inventors: Michael D. Ellis, Boulder, CO (US); Caron S. Ellis, Boulder, CO (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 10/764,287

(22) Filed: Jan. 23, 2004

(65) Prior Publication Data

US 2004/0215958 A1 Oct. 28, 2004

Related U.S. Application Data

(63) Continuation-in-part of application No. 10/645,713, filed on Aug. 20, 2003, which is a continuation of application No. PCT/US02/04847, filed on Feb. 20, 2002.

(60) Provisional application No. 60/270,400, filed on Feb. 20, 2001, provisional application No. 60/442,418, filed on Jan. 25, 2003.

(51) Int. Cl.
*H04M 1/66* (2006.01)

(52) U.S. Cl.
USPC ........... 455/410; 455/411; 455/502; 455/522; 455/425

(58) Field of Classification Search
USPC ................ 455/88, 575.6, 410, 411, 425, 522, 455/502
See application file for complete search history.

(56) References Cited

U.S. PATENT DOCUMENTS

| | | | |
|---|---|---|---|
| 4,637,536 A | 1/1987 | Wong | 224/262 |
| 4,652,141 A | 3/1987 | Arai | 368/278 |
| 4,761,835 A | 8/1988 | Chen | 2/160 |
| 4,803,487 A * | 2/1989 | Willard et al. | 340/7.54 |

(Continued)

FOREIGN PATENT DOCUMENTS

| | | |
|---|---|---|
| DE | 197 12672 | 7/1998 |
| EP | 1018 832 | 7/2000 |

(Continued)

OTHER PUBLICATIONS

Barber et al., "Designing for Wireless LAN Communications," *IEEE Circuits and Devices Magazine*, vol. 12, No. 4, pp. 29-33 (Jul. 1996).

(Continued)

*Primary Examiner* — Kwasi Karikari
(74) *Attorney, Agent, or Firm* — Sterne, Kessler, Goldstein & Fox P.L.L.C.

(57) ABSTRACT

Modular personal networks (MPNs) are disclosed that include multiple devices that may be worn, carried, or used in close proximity to a user. The devices communicate wirelessly. Devices include security circuitry that prevents them from being used in a different MPN once the user has configured them. Devices not designed for use within an MPN can be included in the network using a bridge device. Devices can be integrated into items of jewelry, such as earrings, rings, pendants, and bracelets. One item of jewelry, such as a bracelet, can support multiple replaceable modules with variable functions. Functions of the MPN can include communications, entertainment, medical monitoring, sports monitoring, personal organization, and games. Multiple users each with his or her own MPN can use them to collaborate in creation of music. An MPN can be used for mobile recognition and logging of wildlife.

24 Claims, 22 Drawing Sheets

U.S. PATENT DOCUMENTS

| | | | | |
|---|---|---|---|---|
| 5,059,126 | A | 10/1991 | Kimball | 434/308 |
| 5,148,002 | A | 9/1992 | Kuo et al. | 219/211 |
| 5,243,659 | A | 9/1993 | Stafford et al. | 381/86 |
| 5,391,080 | A | 2/1995 | Bernacki et al. | 434/254 |
| 5,474,083 | A | 12/1995 | Church et al. | 128/733 |
| 5,485,163 | A * | 1/1996 | Singer et al. | 342/457 |
| 5,516,334 | A | 5/1996 | Easton | 482/8 |
| 5,524,637 | A | 6/1996 | Erickson | 600/592 |
| 5,581,492 | A | 12/1996 | Janik | 361/679.03 |
| 5,610,387 | A | 3/1997 | Bard et al. | 235/472 |
| 5,655,028 | A | 8/1997 | Soll et al. | 382/133 |
| 5,684,918 | A | 11/1997 | Abecassis | 386/83 |
| 5,719,743 | A | 2/1998 | Jenkins et al. | 361/683 |
| 5,721,783 | A * | 2/1998 | Anderson | 381/328 |
| 5,757,929 | A * | 5/1998 | Wang et al. | 381/300 |
| 5,781,913 | A | 7/1998 | Felsenstein et al. | 345/169 |
| 5,794,164 | A | 8/1998 | Beckert et al. | 701/1 |
| 5,810,736 | A | 9/1998 | Pail | 600/500 |
| 5,813,009 | A | 9/1998 | Johnson et al. | 707/100 |
| 5,832,296 | A | 11/1998 | Wang et al. | 710/3 |
| 5,844,824 | A | 12/1998 | Newman et al. | 345/156 |
| 5,884,198 | A * | 3/1999 | Kese et al. | 455/575.6 |
| 5,890,074 | A * | 3/1999 | Rydbeck et al. | 455/558 |
| 5,913,163 | A * | 6/1999 | Johansson | 455/426.1 |
| 5,921,890 | A | 7/1999 | Miley | 482/3 |
| 5,925,001 | A | 7/1999 | Hoyt et al. | 600/595 |
| 5,976,083 | A | 11/1999 | Richardson et al. | 600/300 |
| 6,000,000 | A | 12/1999 | Hawkins et al. | 707/201 |
| 6,002,918 | A | 12/1999 | Heiman et al. | 340/7.38 |
| 6,013,007 | A | 1/2000 | Root et al. | 482/8 |
| 6,028,853 | A * | 2/2000 | Haartsen | 370/338 |
| 6,032,108 | A | 2/2000 | Seiple et al. | 702/97 |
| 6,038,542 | A | 3/2000 | Ruckdashel | 705/9 |
| 6,041,023 | A | 3/2000 | Lakhansingh | 369/7 |
| 6,041,214 | A | 3/2000 | Chestnut | 379/211 |
| 6,047,301 | A | 4/2000 | Bjorklund et al. | 708/139 |
| 6,050,924 | A | 4/2000 | Shea | 482/57 |
| 6,078,825 | A * | 6/2000 | Hahn et al. | 455/569.2 |
| 6,091,832 | A * | 7/2000 | Shurman et al. | 381/381 |
| 6,108,197 | A | 8/2000 | Janik | 361/683 |
| 6,128,290 | A | 10/2000 | Carvey | 370/347 |
| 6,140,981 | A | 10/2000 | Kuenster et al. | 345/8 |
| 6,157,533 | A | 12/2000 | Sallam et al. | 361/683 |
| 6,157,824 | A | 12/2000 | Bailey | 455/409 |
| 6,157,935 | A | 12/2000 | Tran et al. | 715/202 |
| 6,164,541 | A | 12/2000 | Dougherty et al. | 235/462.01 |
| 6,181,237 | B1 * | 1/2001 | Gehlot | 340/407.1 |
| 6,212,414 | B1 * | 4/2001 | Alameh et al. | 455/575.6 |
| 6,229,454 | B1 | 5/2001 | Heikkila et al. | 340/870.14 |
| 6,243,573 | B1 | 6/2001 | Jacklin | 455/416 |
| 6,249,427 | B1 | 6/2001 | Carroll | 361/683 |
| 6,272,359 | B1 * | 8/2001 | Kivela et al. | 455/567 |
| 6,282,362 | B1 | 8/2001 | Murphy et al. | 386/46 |
| 6,301,964 | B1 | 10/2001 | Fyfe et al. | 73/1.01 |
| 6,304,459 | B1 | 10/2001 | Toyosato et al. | 361/681 |
| 6,311,071 | B1 * | 10/2001 | Voroba et al. | 455/550.1 |
| 6,314,091 | B1 | 11/2001 | LaRowe, Jr. et al. | 370/338 |
| 6,321,158 | B1 | 11/2001 | DeLorme et al. | 701/201 |
| 6,324,053 | B1 | 11/2001 | Kamijo | 361/683 |
| 6,347,290 | B1 | 2/2002 | Bartlett | 702/150 |
| 6,351,629 | B1 * | 2/2002 | Altschul et al. | 455/90.1 |
| 6,385,434 | B1 | 5/2002 | Chuprun et al. | 455/11.1 |
| 6,388,613 | B1 | 5/2002 | Nagatsuma et al. | 342/357.08 |
| 6,401,085 | B1 | 6/2002 | Gershman et al. | 1/1 |
| 6,427,063 | B1 | 7/2002 | Cook et al. | 434/350 |
| 6,447,424 | B1 | 9/2002 | Ashby et al. | 482/8 |
| 6,449,583 | B1 | 9/2002 | Sakumoto et al. | 702/179 |
| 6,450,922 | B1 | 9/2002 | Henderson et al. | 482/8 |
| 6,477,117 | B1 | 11/2002 | Narayanaswami et al. | 368/251 |
| 6,513,532 | B2 | 2/2003 | Mault et al. | 600/595 |
| 6,560,651 | B2 | 5/2003 | Katz et al. | 709/229 |
| 6,594,370 | B1 * | 7/2003 | Anderson | 381/315 |
| 6,605,038 | B1 | 8/2003 | Teller et al. | 600/300 |
| 6,669,600 | B2 | 12/2003 | Warner | 482/8 |
| 6,678,535 | B1 | 1/2004 | Narayanaswami | 455/557 |
| 6,685,634 | B1 | 2/2004 | Fry | 600/300 |
| 6,736,759 | B1 | 5/2004 | Stubbs et al. | 482/8 |
| 6,741,864 | B2 | 5/2004 | Wilcock et al. | 455/456.1 |
| 6,754,472 | B1 * | 6/2004 | Williams et al. | 455/100 |
| 6,757,719 | B1 * | 6/2004 | Lightman et al. | 709/219 |
| 6,790,178 | B1 | 9/2004 | Mault et al. | 600/300 |
| 6,876,845 | B1 | 4/2005 | Tabata et al. | 455/344 |
| 6,934,461 | B1 | 8/2005 | Strub et al. | 386/46 |
| 6,947,571 | B1 | 9/2005 | Rhoads et al. | 382/100 |
| 7,130,664 | B1 * | 10/2006 | Williams | 455/567 |
| 7,162,392 | B2 | 1/2007 | Vock et al. | 702/82 |
| 7,203,721 | B1 | 4/2007 | Ben-Efraim et al. | 709/203 |
| 7,229,385 | B2 | 6/2007 | Freeman et al. | 482/4 |
| 7,261,564 | B2 | 8/2007 | Sutula, Jr. | 434/150 |
| 7,549,947 | B2 | 6/2009 | Hickman et al. | 482/8 |
| 2001/0003542 | A1 | 6/2001 | Kita | 381/334 |
| 2001/0011025 | A1 * | 8/2001 | Ohki et al. | 455/556 |
| 2001/0049470 | A1 | 12/2001 | Mault et al. | 600/300 |
| 2002/0000470 | A1 * | 1/2002 | Lanzaro et al. | 235/462.45 |
| 2002/0022551 | A1 | 2/2002 | Watterson et al. | 482/8 |
| 2002/0068604 | A1 * | 6/2002 | Prabhakar et al. | 455/556 |
| 2002/0091843 | A1 * | 7/2002 | Vaid | 709/230 |
| 2002/0094845 | A1 * | 7/2002 | Inasaka | 455/566 |
| 2005/0113650 | A1 | 5/2005 | Pacione et al. | 600/300 |

FOREIGN PATENT DOCUMENTS

| | | |
|---|---|---|
| EP | 1 050 793 A2 | 11/2000 |
| GB | 2350 749 | 12/2000 |
| JP | 5-249899 A | 9/1993 |
| WO | WO 87 05229 | 9/1987 |
| WO | WO 98 38820 | 9/1998 |
| WO | WO 00 36900 | 6/2000 |
| WO | WO 01 00281 | 1/2001 |

OTHER PUBLICATIONS

Bhagwat et al., "A routing vector method (RVM) for routing in Bluetooth scatternets," *Mobile Multimedia Communications*, pp. 375-379 (Nov. 1999).

Bukhres et al., "Mobile computing in military ambulatory care," Computer-Based Medical Systems, pp. 58-63 (Jun. 1997).

Hum, "Fabric area network—A new wireless communications infrastructure to enable ubiquitous networking and sensing on intelligent clothing," *Computer Networks*, vol. 35, issue 4, pp. 391-399 (Mar. 2001).

Jones et al., "A Protocol for Automatic Sensor Detection and Identification in a Wireless Biodevice Network," Eleventh IEEE Symposium on Computer-Based Medical Systems, pp. 311-316 (Jun. 12, 1998).

http://grouper.ieee.org/groups/802/11/.
http://wearcam.org/ieeecomputer/r2025.htm.
http://www.bluetooth.com/index.asp.
http://www.cnn.com/2000/TECH/computing/08/18/wired.jacket.idg/.
http://www.cnn.com/2000/STYLE/fashion/06/26/wearable.computers/index.html.
http://www.digiman.org/html/main.html.
http://www.fitsense.com/.
http://www.techtv.com/freshgear/products/story/0,23008,3342589.html.
http://www.via-pc.com/index.htm.

* cited by examiner

MODULAR PERSONAL NETWORK SYSTEMS AND METHODS

CROSS-REFERENCE TO RELATED APPLICATION

This application is a continuation-in-part application of U.S. patent application Ser. No. 10/645,713, filed Aug. 20, 2003, which is a continuation application of International Application No. PCT/US02/04947, filed Feb. 20, 2002, which is hereby incorporated by reference herein in its entirety and which claims the benefit of U.S. Provisional Patent Application No. 60/270,400, filed Feb. 20, 2001. This application also claims the benefit of U.S. Provisional Patent Application No. 60/442,418, filed Jan. 25, 2003, which is hereby incorporated by reference herein in its entirety.

FIELD OF INVENTION

The present invention relates to modular personal network systems and methods, and, in particular, to wireless networks of individual components that can be easily added to or removed from a network to change the network's functions, and in which the individual components are worn, carried, or used on or about the person of the user.

BACKGROUND OF THE INVENTION

A Modular Personal Network, or MPN, is a network of personal devices, each of which is designed to optimally perform a specific task, creating a system that is greater than the sum of its parts. Examples of MPNs are illustratively disclosed in WO 02/067449, "Modular Personal Network Systems and Methods", to Ellis et al, which is hereby incorporated by reference herein in its entirety.

A number of improvements to the MPN are desired. MPN users need an improved method of providing security in the MPN and its components, so that individual components cannot be used in an MPN other than the one for which they were configured.

MPN users may have existing devices, such as digital cameras, mobile telephones, MP3 players, and personal digital assistants that were not designed for use within an MPN. Such users may need a device that can provide a communications bridge between an MPN and such a preexisting device.

Wildlife enthusiast have a need for an improved system to recognize and log wildlife animal and plant sightings, as well as to upload the logs to a personal computer and to compare them with the logs of other enthusiasts.

Musicians may desire a personal network of individual devices to use in the creation of music. Further, some musicians desire a system that facilitates musical collaborations.

Some MPN users may be interested in individual network components that can be worn unobtrusively, and which may have a pleasing appearance. Such users may desire an MPN individual network component (INC) that can functions as an item of jewelry. Some of these users may be interested in modular jewelry systems, in which individual modules, such as links in a bracelet, may be added at any time. These users may be interested in a modular system that provides added electronic functions with the addition of each new jewelry module into the system.

SUMMARY

In accordance with the principles of the present invention, modular personal networks and methods are provided.

MPN concepts may be illustratively explained based on the parts of its name:

Modular: Each device provides one or more functions to the network. A new device can be added at any time, increasing the capabilities of the system, for example, without losing anything that already is supported. A single device (e.g., any single device) can be removed, for example, at any time, resulting in a system that can perform without that device (e.g., one less function), but which still works well as a system.

Individual devices can be swapped out, for example, at any time. For example, a user may decide that a green display goes better with today's outfit than yesterday's blue display. The new display can be substituted without impacting any of the other devices, and without reducing any of the functions of the system.

The network protocols may, for example, be "open", which means that new devices with new capabilities can be designed at any time and brought into the network. This approach allows the network to perform functions that were not imagined at the time it was originally created.

Personal: The devices are small and designed to be carried or worn by a user. As such, they may be worn at the waist, around the wrist, mounted to an item of clothing, carried in a pocket or purse, or mounted to a piece of the user's personal equipment, etc. The network is preferably unobtrusive and may not even be noticed by other individuals. The entire network is preferably about the same size as the user's "personal space". Each device may, if desired, be further personalized, so that it only functions in its user's network.

The MPN can also be considered personal because it can provide exactly the design and functions that the user wants at any particular time. An advantage of this technique is that users no longer have to live with the limited set of functions that some manufacturer decides is the best combination. If the user needs something new, he can preferably just get the new component and add it to the network. If the user no longer wants a particular feature, components can preferably be removed one at a time. If the user wants to mix and match, the combinations can be unlimited. If desired, in some instances, one or more components that are not "personal" may be added to an MPN.

Network: The devices in the MPN preferably communicate using a low-power, short-range wireless network, for example at a 2.4 GHz radio frequency. Each device preferably has a range of a few meters for messages to and from other devices in the network. Any device can preferably talk to any other device in the MPN, using, for example, a standard protocol.

An advantage of the MPN can be the ability for the user to add or remove individual network components (INCs) while maintaining the integrity of the network. If the INC is of a known type and the desired new function is already defined, a new INC can preferably be added on the fly, simply by bringing into proximity of the network. If it's a new type of INC, or if a new function is desired from an INC already in the MPN, the new functionality can preferably be downloaded into the MPN.

There are two types of MPN that are illustratively described herein. The first type has a control unit as one of the INCs. The control unit is the hub of the MPN. It communicates with all of the other INCs and coordinates the functions of the network. The second type of MPN has distributed control. With distributed control, each of the INCs provides its own control, and all INCs operate as peers.

The user's PC can be a base (e.g., the only base) from which the user configures and manages the MPN. There may be an application that runs on the PC, and which controls the functions of the MPN. If there is a control unit, the PC may communicate only with it. The PC might alternatively communicate instructions to all of the INCs.

If the PC has a wireless transceiver card, it can communicate with MPN INCs using the INCs' wireless network (effectively becoming another device in the MPN). If desired, the INC may have a wired port, such as a USB port, which can be connected to the PC. Or, the PC can have a docking station into which the INC can be connected directly. The user connects the PC to the INC and can run the MPN PC application whenever he or she wants to control the MPN.

Some types of communication that can take place between the PC and the MPN INC may, for example, include:

The PC can download a new driver into a control unit to control a new type of INC.

The PC can download a new software module into the control unit to support a new function using existing INCs.

The PC can download new software into any INC to control its functions.

The PC can download configuration parameters, or the current time, into the Control Unit or any other INC.

The PC can download music or other media into the control unit for playback.

The PC can download any other type of data into an INC.

The PC can upload collected data from the control unit or other INC.

The MPN PC application supports plug-ins to handle unanticipated types of INCs. For example, the application itself can handle generic downloading of software and data, and the plug-in can handle specific new functions. This may include configuration of specific INC parameters, uploading of new types of data, displaying, processing, and storing uploaded data, or any other functions specific to the new INC.

MPN devices (e.g., all MPN devices) preferably use a standard protocol for messages within the network. This protocol may be built on top of an industry standard wireless protocol, such as IEEE 802.15. The vast majority of the communication to and from any INC is with other INCs in the same network, and the protocol is preferably optimized for this.

Preferably every MPN is assigned an identifier that is unique to that MPN, and each message within that MPN is preferably tagged with that identifier. This allows INCs to determine whether a message it receives originated within its own MPN, or whether it has received a stray message from another MPN.

Preferably, each INC in the MPN has an identifier that is unique within that network. Individual INCs (e.g., each INC) may maintain a table of other INCs in the network that it may send messages to or receive messages from. A standard table of INC types, manufacturers, and capabilities may be built into all INCs, and the table may be augmented with data downloaded from the PC as new types of INCs are supported.

INCs of the same type may use the same protocol messages. For example, two different types of display INCs built by different manufacturers would accept and process the same types of messages to display information graphically. Standard messages are also defined to query the specific capabilities of an INC. For example, a control unit might query a display INC to determine its pixel resolution, availability of colors, and other features.

When a user creates a new MPN (by buying the first component or "starter kit") the MPN will preferably be programmed with a unique MPN lock. For example, the package with the MPN application to be loaded on the PC would include a "lock number," a unique sequence of letters and numbers. The first time the user connects the INC to the PC, the application would prompt for the lock, and for a new password from the user. The application would then download the lock into the INC. The INC would store the encrypted lock in a secure memory on the INC.

As the user adds new INCs to the network, each would preferably be programmed with the same lock. If desired, the application could store the lock on the PC, and only require the user to enter the password (and not the lock) each time a new INC is added to the MPN.

Once in an INC's memory, the lock value is preferably stored in secure memory and cannot be retrieved. If the user wishes to remove an INC from the network and give it to someone else to install in another network, the PC application can for example allow the user to delete the lock from the INC by typing in the original lock value and password.

If the user loses the original lock value or password, the INCs can still be used together. However, in some embodiments, new INCs cannot be added to the network because of the lost lock value or password. In such instances, an authorized repair facility may have a method to clear the lock from secure memory, so that the user could add the INCs into a new MPN with a new lock value. The clearing of secure memory may be done in person, by sending the device(s) to the repair facility, or over the Internet using security controls such as passwords, PINs, etc.

Each time an INC is brought into the MPN, the other INCs (e.g., one or more of them) may query it to ensure the locks match. The lock value may be sent in an encrypted format so that it cannot be stolen. In another technique, a "key" value can be sent from the new INC, and the other INCs can use the key to try to open the lock. The required key value may be varied based on the time, the sending or receiving INC, or other criteria, so that a stolen key cannot be used at a later time.

If desired, the lock value can also be used to derive the unique MPN identifier, used to tag messages sent between INCs in the network.

Each INC in the MPN is preferably individually powered. The battery may be a single-use, long-life power source. Rechargeable batteries may also be used, which may be automatically recharged when the user plugs the INC into the PC or the docking station at the PC.

Each INC preferably includes power-monitoring circuitry. The communication protocol may include messages to report low power conditions. The complete loss of power in an INC (e.g., any INC) can preferably be predicted before it happens and reported to the user. If an INC loses its power, it will preferably be handled gracefully, for example, similar to the removal of the INC from the network.

The MPN preferably includes a global power-off and power-on feature. For example, when an airline passenger is using electronic devices he must shut all of them off as the airplane approaches landing. The MPN user will turn off one INC. That INC will broadcast a message to all of the other INCs in the MPN. Each INC will then store any temporary status information, stop all wireless transmissions, and go into a low power consumption state. All of the INCs will remain in this state until the user turns one of the INCs (e.g., the first INC) back on. This INC will broadcast a resume message, and all of the INCs in the MPN will resume normal functions. In this example, if desired, a complete shutdown of INCs may also be applied.

Some INCs and features may also have timeout features, in which they automatically go into a low power consumption state after a defined period of inactivity.

The functions of every MPN INC preferably include a number of standard functions. The use of a standard "reference design" with standard components can significantly reduce the cost of every INC. An application specific integrated circuit (ASIC) designed specifically to encapsulate these common functions can, for example, allow a compact, low-cost design of new INCs. It can also help to ensure compatibility between INCs, and to create a common set of user expectations.

Some of the common functions that may be encapsulated, for example, include:
  Wireless transmission and reception
  Low-level and high-level protocols
  Protocol extensions capability (memory and processor, for example)
  Power management
  Secure memory and lock/key handling
  Standard device types, manufacturers, and capabilities Some capabilities may be used in many but not all INCs. These capabilities would also benefit from reference designs and standard components. These capabilities, for example, include:
  PC communication protocol
  Extended processor and memory for more advanced functions There may be several types of INCs that will be present in a large percentage of MPNs. These, for example, may include:
  Control Unit: Can be considered the general-purpose processor for controlling the functions of the MPN. It preferably includes a processor and memory. The memory can be used for downloading software modules to control the other INCs and performing specific functions. It may also be used for storing digital music, or other types of media, to play back for the user, or which the user has captured. It may also be used for collecting data from the other INCs. The control unit may be worn on the waist, worn on a wristband, or carried in a pocket or purse, etc. Memory can be of any type or combination of types, such as RAM, hard disk, CD-ROM, mini-disk, flash memory, and may be permanent or removable.
  Display: The display will typically be a general-purpose graphical display device, such as an LCD. It may, for example, be worn on the wrist.
  Audio Output: An audio output (such as headphones) may often be included.
  User Input: User inputs (e.g., buttons) may be included separately and/or on any of the other INCs, such as the control unit or display. There may also be separate user controls to support some features. These could include microphone input, pen-based input, a keyboard, or any other appropriate portable input device.
  Phone: A mobile phone or other communications device can be included as an INC in the network. The actual INC may be minimal, as the phone features may use the functions of the control unit, display, audio output, and user control, rather than duplicating those functions.
  Other common INCs, for example, include a digital camera, GPS receiver, and a heart rate monitor.

There may also be common collections of functions into single INC. For example, there may be combination control/display/user input INCs.

If the user has an existing device, such as a mobile phone, personal digital assistant (PDA), MP3 player, or digital camera, that is not MPN-ready, that device may still be incorporated into the MPN. One of the MPN INCs, for example the control unit, may have a USB port or other type of connector to interface with the existing device, and it may be able to accept downloaded software to interact with the existing device.

For example, the existing device may be an MP3 player or a digital camera with a USB port, originally designed to interface with a PC. The control unit may have a USB port. Software downloaded into the control unit may enable it to access the features of the existing device over the USB port, for example to download music into the MP3 player or to upload digital photographs from the digital camera.

If the existing device is a mobile telephone, the control unit may have a port that allows access to the accessory port on the phone to access its functions, for example to send audio to the phone, to get audio from the phone, to dial, or to perform other functions. If the existing device is a PDA, the control unit may have a port and software that allow access to functions of the PDA, using the PDA synchronization port that was originally designed to interface with a personal computer.

The control unit or other MPN device that is connected with the existing device may use its wireless transceiver to make the functions of the existing device available to other INCs in the MPN.

With the use of a standard design and a public protocol, any manufacturer can build INCs to be used in any MPN. There would likely be a certification process to ensure that new INCs are truly compatible and interoperable.

Establishing interoperability allows a user to buy any combination of INCs of different types from different manufacturers, and count on them to work together correctly. A user can even have INCs of the same type from different manufacturers, and use them at different times. This would allow a user to shop for the best bargain for any INC or set of INCs.

If an INC fails, it can preferably be replaced with the same type of INC, or with a different INC providing similar capabilities.

When the MPN is connected to a PC, the MPN can preferably communicate with the outside world, using the PC's Internet connection (e.g., under the control of the application on the PC). This, for example, allows a number of types of interaction:
  The PC can download updated software to control INCs or provide new features.
  Control commands or configuration parameters can be provided for the MPN from a doctor, coach, therapist, etc.
  A service technician can diagnose problems in the MPN. The service technician can also remotely clear the secure memory in an INC.
  Data from the MPN can be shared with other computers on the Internet.
  Two MPN users can share data between their networks.

If desired, sharing of data can also happen directly when two MPN users are in close proximity. For example, by extracting the unique MPN identifier from a message sent by an INC of another MPN, a message can be addressed back to an INC of the other MPN. This can allow features such as multi-player games and competitions, sharing of personal data, sharing of media files, sharing of software, etc.

An MPN can include a communication INC, such as a mobile phone, as one of the INCs in the network.

MPN devices may be packaged in a number of ways, including for example:
  Starter kit: This kit includes the MPN PC application, a security lock value, and some basic INCs (control unit, display, etc.) It may include a link to a website to find updated plug-ins, drivers, device lists, etc. There may also be coupons for other MPN products offered by the same manufacturer.

Device kit: This kit includes a specific INC. If appropriate, it may also include a plug-in and driver to control and configure the INC.

Feature kit: This kit includes the items necessary to implement a specific feature. It may include one or more INCs. It may include a plug-in for the feature. It may include one or more updated drivers. It may also include web links to get updates.

Multi-purpose device: Some manufacturers may choose to create single INCs capable of performing several functions.

Adapter kit: This kit includes the items necessary to adapt a non-MPN device to be used in an MPN. It may include a specialized control unit, an adapter cable, a software plug-in, downloadable software, or other appropriate items.

One method of making a wearable INC is to incorporate it into an item of jewelry, so that it provides an aesthetically pleasing form when worn by a user. It may not even be obvious to anybody other than the wearer that the item is anything other than pure jewelry.

For example, an INC can be incorporated into an earring or otherwise designed to be worn in a pierced body part. An earring INC may include, for example, a wireless receiver and a speaker. This would allow other INCs to send audio content to be played in close proximity to the user's ear, at a low and unobtrusive volume. Another example of an earring INC is to include an antenna for a GPS receiver or a mobile telephone. The received signal may be remodulated and sent to another INC for processing.

An INC may be worn as a pendant around the neck. The pendant may be any appropriate INC, such as a control unit, a display device, a user input device, a GPS receiver, or may provide any other suitable function or combination of functions.

An INC may be worn as a ring or may be included as part of a ring. The ring INC may include a user input device such as pushbutton or a microphone. The ring INC may include any other type of device such as a digital camera, a pulse oximeter, a blood pressure sensor, a simple display device, etc.

An INC incorporated into any number of jewelry items including, but not limited to: a brooch, cufflinks, tie tack, tuxedo studs, barrette or other hair accessory. An INC may be included in eyeglass temples (for example as an antenna or a speaker).

Another type of jewelry that may include one or more INCs is the modular jewelry system, such as a modular bracelet or charm bracelet. A modular bracelet is designed to allow the user to add or remove individual links at any time. A charm bracelet allows individual charms to be added or removed at any time. Any of the modular links or charms may include a wireless transceiver and provide the functions of any appropriate INC. Each new modular link or charm may add similar capabilities, such as an additional amount of memory, or they may each add a different type of capability. For example, one charm may include a processor to act as a control unit, a second charm may provide memory, a third charm may provide an input sensor (such as a temperature sensor), and a fourth charm may be a user input device.

If multiple modules are added to a modular jewelry system, they may act as a single INC. For example, one of the jewelry modules may provide the wireless transceiver that is used by all of the other jewelry modules. Or, the base system without any added jewelry modules may include the wireless transceiver, power source, processor, memory, and any other electronics required to interact within the MPN, and each added jewelry module may include only the electronics required to add a specific new function. The modular jewelry system itself may act as the communications bus for transferring data among the jewelry modules in the system.

In fact, the modular jewelry system may be capable of providing functionality without any other INCs. In this case, the system can provide any new functions simply by attaching a new jewelry module to the base system.

A number of functions can be supported even with the most basic MPN hardware. These, for example, include:

Time functions, such as a wristwatch

Personal organizer functions, such as appointment notification and contact information (synchronized with data on the user's PC)

Music playback

Personal information exchange with another MPN

Games (single user or with another MPN)

The MPN can provide a mobile wildlife recognition and logging system. Prior to an excursion, the user can download into an INC in the MPN a library of information about flora and fauna of a particular region. This can include photos, audio sample of animal calls, information about habits and territories, and text descriptions. If desired, the library can be loaded in on a mini-disk or other removable data storage device.

During the excursion, the user sees an animal or plant of interest, and takes a picture using a digital camera INC connected to the MPN. An audio sample can also be taken using an INC. The MPN can use the image, the audio sample, location information, time of day, current weather conditions, or other factors to determine one or more likely matches from the wildlife library. These likely matches are presented to the user on a display INC, and the user can make the final determination. The user uses the images, audio samples, and other data from the possible matches to make the determination, or can narrow it down to the most likely matches. The MPN keeps a log of what wildlife was seen when and where, which can be reviewed on the MPN, and can be uploaded later to the PC.

This feature may be of particular interest to birdwatchers, who can use this system to keep their bird watching diaries electronically. The system may support comparison of logged sightings between multiple birdwatchers.

The MPN can provide features for musicians. For example, a musician can have INCs for microphones and speakers, an INC to store music, an INC to convert stored music from one format (e.g., Midi) to audio for output, an INC to perform audio processing and special effects, an INC to mix multiple inputs, and an INC to display sheet music.

Multiple musicians, each with an MPN, can use features of the MPN to play together. For example, messages sent between the systems can coordinate the timing and the playing of a single piece of music. Multiple audio inputs can be received by components of the MPNs and mixed and stored into a single INC. The recorded music can be uploaded to a PC or other music processing system for later processing.

BRIEF DESCRIPTION OF THE DRAWINGS

Further features of our invention, its nature and various advantages will become more apparent upon consideration of the following detailed description, taken in conjunction with the accompanying drawings, in which like reference characters refer to like parts throughout, and in which.

DETAILED DESCRIPTION

Figure 1:
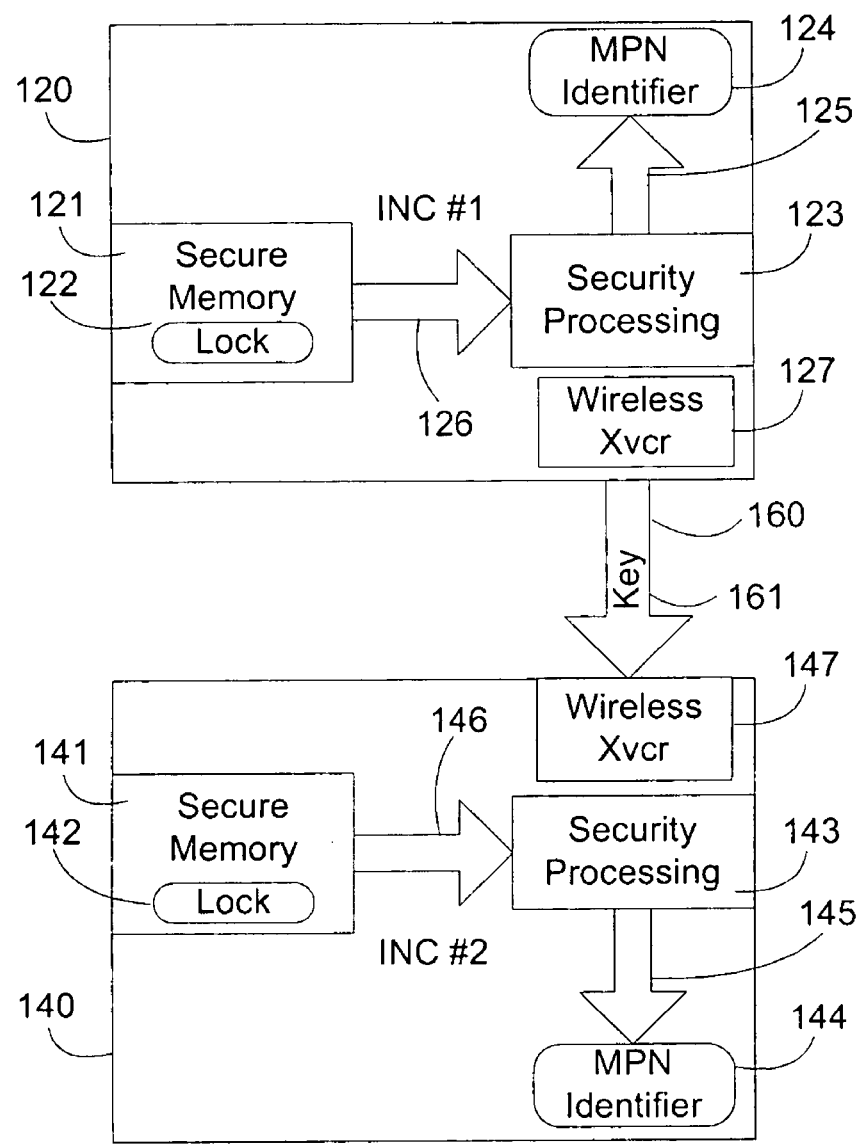
FIG. 1 is a block diagram of two INCs within an MPN that provide secure processing.

FIG. 1 shows illustrative modular personal network (MPN) 100. MPN 100 includes individual network component (INC) 120 and INC 140. Each INC includes a wireless transceiver, such as wireless transceiver 127 and wireless transceiver 147, or in some cases a wireless receiver or wireless transmitter. The INCs communicate over wireless path 160.

Each INC 120 and 140 has secure memory 121 and 141, in which a lock value 122 and 142 is stored. Each INC also includes security-processing circuitry 123 and 143. The security-processing circuitry accesses the lock value from secure memory over secure path 126 or 146. The secure memory may be designed so that stored information, such as the lock value, cannot be retrieved except by the security-processing circuitry, and may require the use of an access code. The security-processing circuitry may use the retrieved lock value to determine the MPN identifier 124 and 144 of the INC. The MPN identifier may be used to tag messages sent between INCs, so that each INC only responds to messages that originated from another INC in the same MPN.

When an INC, such as INC 120, is added to an MPN, it may send a key value 161 to INC 140. Security-processing circuitry 143 in INC 140 may use received key value 161 and lock value 142 to determine whether INC 120 is a legitimate component in MPN 100.

Figure 2:
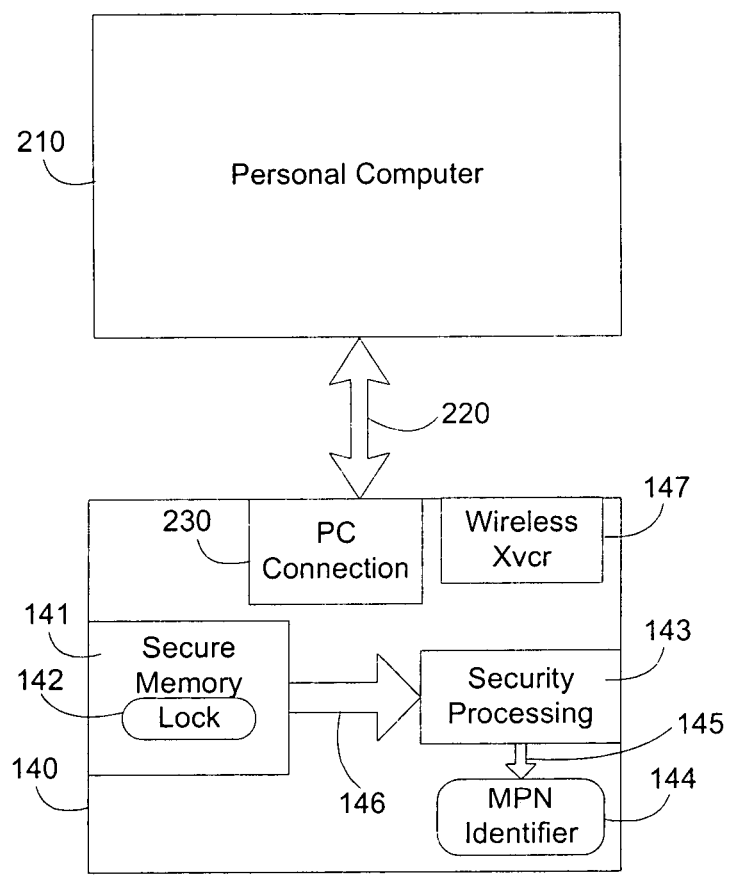
FIG. 2 is a block diagram of a personal computer providing configuration of security functions within an INC.

FIG. 2 shows how personal computer (PC) 210 may communicate with INC 140 over communications path 220. INC 140 may have PC connection 230, which may be a wired connection such as a serial port or USB port, may be the same as wireless transceiver 147, or may be any other suitable wired or wireless connection. For example, PC 210 may download a driver into INC 140 to control another INC. As another example, PC 210 may download a new software module into INC 140 to supplement or replace existing software, to add a new function to INC 140 or to modify an existing function in INC 140. As another example, PC 210 may download configuration parameters to INC 140. As another example, PC 210 may send the current time to INC 140. As another example, PC 210 may download digital audio or other media (such as images and video) to INC 140. As another example, PC 210 may download any other type of data to INC 140. As another example, PC 210 may upload media data that may have been captured by INC 140, such as audio, video or still images. As another example, PC 210 may upload any other type of data that may have been collected by INC 140, such as location data, speed data, heart rate data, or medical data. As another example, PC 210 may allow another computer to access data on INC 140 or download data to INC 140, using a network such as the Internet. This may include allowing a doctor, therapist, or coach to download instructions to INC 140 and to upload data from INC 140. It may also include allowing a service technician to remotely access INC 140 for configuration, upgrade, troubleshooting, and other maintenance functions. A user may also be able to access data and software upgrades on the Internet and download them into INC 140 from PC 210.

Figure 3:
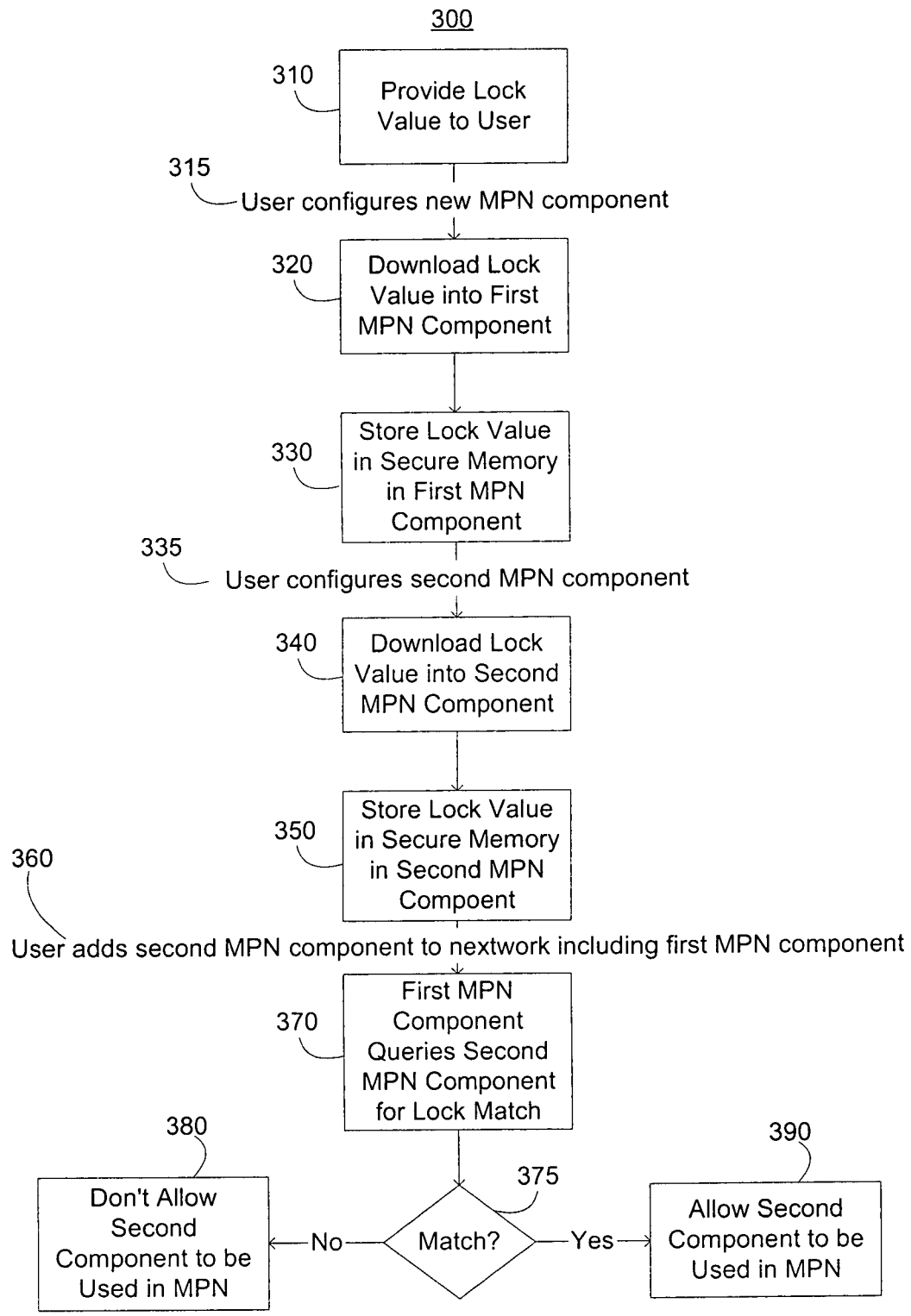
FIG. 3 is a flowchart of an illustrative process showing how security can be provided within an MPN.

As another example, PC 210 may perform security functions with INC 140. This is illustrated by flowchart 300 in FIG. 3. Some steps in flowchart 300 may be optional or may be performed in a different order. In step 310, a lock value may be provided to a user. For example, the user may purchase an MPN starter kit. The starter kit may include one or more INCs, one of which may be a control unit. The starter kit may also include other items, such as PC software that may be used to interface with the INCs of the MPN. If the INCs have a wired connection to the PC, the starter kit may include a cable to make the connection, such as a serial cable or a USB cable. The starter kit may also include a lock value. The lock value may be unique to the starter kit—each starter kit may have a different lock value. If desired, the starter kit may not include any INCs—they may be sold separately.

In step 315, the user may configure an INC, such as INC 140 using PC 210. INC 140 may have been purchased as part of a starter kit, or it may have been purchased separately. The user may use a cable that was purchased with the INC, with the starter kit, or purchased separately. If the connection between PC 210 and INC 140 is wireless, the user may put INC 140 into proximity of PC 210. The user may load software onto PC 210 that was, for example, purchased with INC 140 or with the starter kit, and the user may use the loaded software to configure INC 140. If desired, the user may load a plug-in that was purchased with INC 140 to augment software that was purchased with the starter kit. The user may then use the software loaded on PC 210 to load software and configuration data into INC 140. One of the types of configuration data that may be loaded into INC 140 is the lock value. This may be the lock value that was purchased as part of the starter kit. In some embodiments, rather than loading the lock value itself, a value derived from the lock value using any suitable algorithm may be loaded. The software loaded onto PC 210 may prompt the user to enter the lock value. It may also prompt the user for a password. The first time the user enters the lock value, the user may be prompted to create a new password and to confirm it. The software may store the lock value and the password, in an encrypted format, on PC 210's disk drive or other storage device. PC 210 may send, in step 320, the lock value, or a value derived from the lock value, to INC 140 over communication path 220.

In step 330, the lock value or the value derived from the lock value may be stored in secure memory 141 in INC 140. The lock value may be transmitted in encrypted format, it may be encrypted by security-processing circuitry 143, or it may be stored in unencrypted format.

In step 335, the user may configure a second INC, such as INC 120 of FIG. 1. INC 120 may have been purchased along with INC 140, may have been purchased as part of a starter kit or other package, or may have been purchased separately. INC 120 may be connected to PC 210 of FIG. 2 using the same means as was used to connect INC 140. INC 140 may be configured using the same software on PC 210, different software on PC 210, or using the same software and with a plug-in that was purchased along with INC 120. Configuration of INC 120 may include downloading software to INC 120. It may include downloading software to one or more additional INCs, such as INC 140, which may be a control unit. Configuration may also include downloading configuration settings to INC 120, INC 140, or any other INCs that are included in the same MPN.

As part of the configuration of INC 120, the lock value may be downloaded into INC 120, in step 340. The user may be prompted for the password to enable the download of the lock value (or the value derived from the lock value). If desired, the lock value may have been previously stored on PC 210, so that the user does not have to reenter it when configuring new INCs for the same MPN. If desired, the software running on PC 210 may track the lock values associated with multiple MPNs, and may allow the user to name each MPN so that it can be later referred to without having to remember the individual lock values for each.

After the lock value or derived value is sent to INC 120 over communication path 220, it may be stored in secure memory 121, in step 350. The lock value may be transmitted in encrypted format, it may be encrypted by security-processing circuitry 123, or it may be stored in unencrypted format.

The user may, at some point after configuring INC 140, be using it as part of MPN 100. The user may wish to begin to use INC 120 as part of MPN 100, in step 360. When INC 120 is brought into proximity of INC 140, there may be a check for a match between the components. INC 140 may send a query to INC 120 for identifying information over communication path 160, in step 370. INC 120 may send identifying information to INC 140 over communication path 160. The identifying information may include a unique MPN identifier. The MPN identifier may be stored in the INC, or it may be derived from the lock value. The identifying information may include the lock value. However, sending the lock value may not be secure. The identifying information may include a key value 161. On receipt of the key value, INC 140 may use a security algorithm to check for a match with the lock value stored in secure memory 141, in step 375.

The key value may be fixed for each lock value, or for each combination of lock value and INC. Alternatively, it may be varied over time so that a stolen key value cannot be used at a later time.

If there is no match, then in step 380 INC 140 may disallow the use of INC 120 in MPN 100. Other types of communications may still be allowed between INC 120 and INC 140, where the communications are of types appropriate between different users. This may include exchange of data, playing games, etc.

If there is a match, then in step 390 INC 140 may allow the use of INC 120 in MPN 100. This may include INC 140, and possibly other INCs in MPN 100, recording identifying information about INC 120 in local memory, so that subsequent communication may proceed without further query. If desired, INC 120 may also store information about INC 140 and other INCs in MPN 100.

Figure 4:
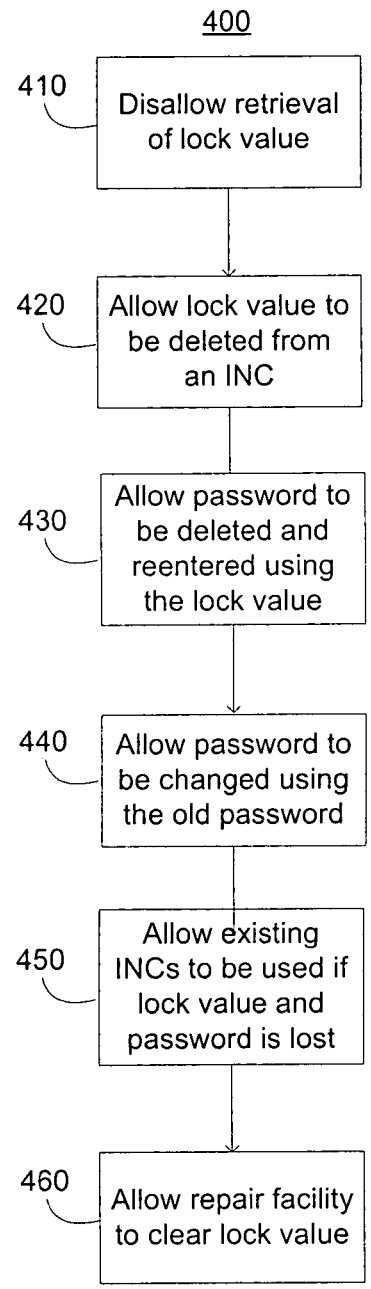
FIG. 4 is a flowchart of an illustrative process for providing security maintenance functions for an MPN.

FIG. 4 shows a flowchart 400 for providing security maintenance functions for the MPN. Some steps in flowchart 400 are optional and the steps may be performed in any suitable order. In step 410, the system may disallow the retrieval of the lock value. This may include the storing of the lock value in encrypted format within PC 210, within each INC, and while it is being transmitted between the PC and various components in the MPN.

In step 420, the system may allow a lock value to be deleted from an INC. For example, a user may wish to remove an INC from his or her MPN and give the INC to someone else for use in another MPN. The software loaded on PC 210 may request the password from the user, and send a command to the INC to clear the lock value from its secure memory.

The user may at some point lose or forget the password and/or the lock value, or wish to change the password. If the user loses the lock value, they can continue to add and remove INCs from the MPN using the password. If the user forgets the password, the software may allow the user to create a new password by entering the lock value in step 430. If the user wishes to change the password and remembers the old password, the software may allow the user to enter a new password by first entering the old one in step 440. If the user loses both the lock value and the password, existing INCs can continue to be used in the MPN, but new INCs cannot be added, and the INCs cannot be removed from the MPN to be added to another MPN, in step 450. However, an authorized repair facility may be able to delete the lock value from an INC, in step 460. For example, the user may deliver the INC to the repair facility, or it may be performed over the Internet, with appropriate security precautions. Other techniques may also be used if desired.

Figure 5:
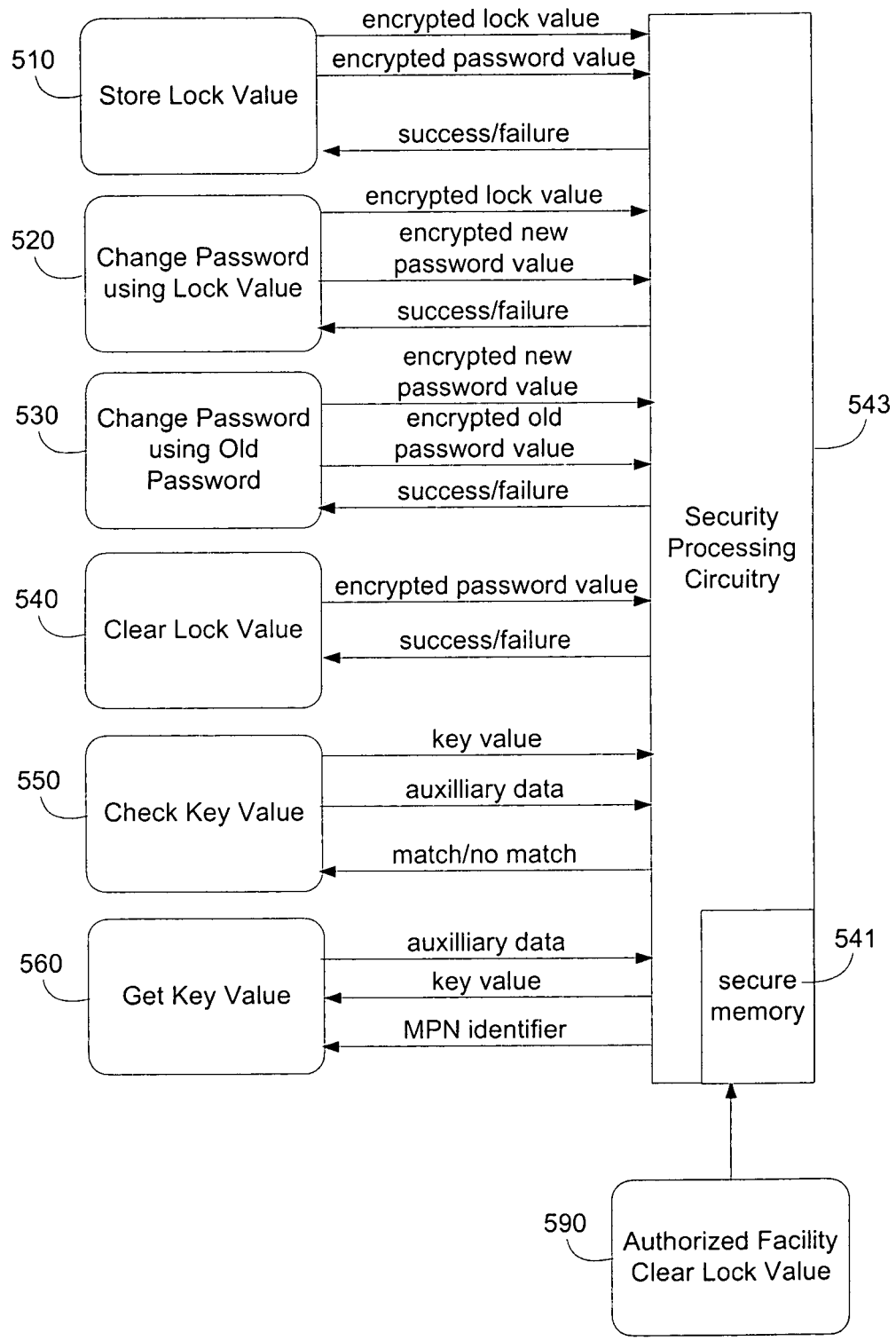
FIG. 5 is a block diagram of the functions provided by the security-processing circuitry within an INC.

FIG. 5 shows more detail of the functions that may be provided by security-processing circuitry 543. In function 510, a lock value may be stored in secure memory 541 by security processing circuitry 543. Function 510 may provide the lock value in encrypted format as well as the user-specified password, which may also be encrypted. Security-processing circuitry 543 may store the encrypted lock value and password. If the storage operation is successful, which will typically be true if there isn't already a lock value and password stored, it will return an indication of the successful completion of the operation. If the storage operation is unsuccessful, for example if there is already a lock value and password stored in secure memory 541, an indication of the failure of the operation may be returned.

In function 520, the password stored in secure memory may be changed. The new password value, which may be encrypted, may be provided, along with the encrypted lock value for confirmation. If the operation is successful, i.e. if the provided lock value correctly matches the lock value stored in secure memory 541, the new password may be stored into secure memory 541, replacing the existing password. If the provided lock value does not match, an indication that the operation was unsuccessful will be returned.

In function 530, the password stored in secure memory may be changed. The new password value, which may be encrypted, may be provided, along with the old password value for confirmation, which may also be encrypted. If the operation is successful, i.e. if the provided old password value correctly matches the password value stored in secure memory 541, the new password may be stored into secure memory 541, replacing the existing password. If the provided old password value does not match, an indication that the operation was unsuccessful will be returned.

In function 540, the lock value and password stored in secure memory may be cleared. The password value, which may be encrypted, may be provided. If the operation is successful, i.e. if the provided password value correctly matches the password value stored in secure memory 541, the password and lock value may be cleared from secure memory 541, allowing the INC to be programmed with a new password and lock value. If the provided password value does not match, an indication that the operation was unsuccessful will be returned. If desired, this function may accept the lock value as a substitute for the password value, or it may require both the password and the lock value.

In function 550, a key value from another INC may be checked to see if it matches the lock value stored in secure memory 541. The key value, along with any desired auxiliary data may be provided. Auxiliary data may include, for example, the current date or time, the identifier of the other INC, the identifier of this INC, or any other suitable value(s). The security-processing circuitry 543 may use the provided data along with the stored, encrypted lock value, to determine if there is a match. If the provided key value does not match, an indication that the operation was unsuccessful will be returned. In one implementation, the security-processing circuitry 543 may use an asymmetric encryption algorithm, with the provided key as the public key, and the encrypted lock value using the private key.

In function 560, the security-processing circuitry 543 may return the public key value associated with its lock value. It may use provided auxiliary data, such as the current time or the INC's unique identifier, or any other suitable information. This function may also return a unique identifier for the MPN. It may also return a unique identifier for the INC.

Security-processing circuitry 543 may also support a maintenance function 590 that can only be accessed by an authorized repair facility to clear the lock value and password stored in secure memory 541. It may require the presence of specific codes or signals that are only available at an authorized repair facility.

Security-processing circuitry 543 and secure memory 541 may be standard part of the design of all MPNs. If desired, these circuits may be incorporated into an application-specific integrated circuit, to ease design and reduce costs.

Figure 6:
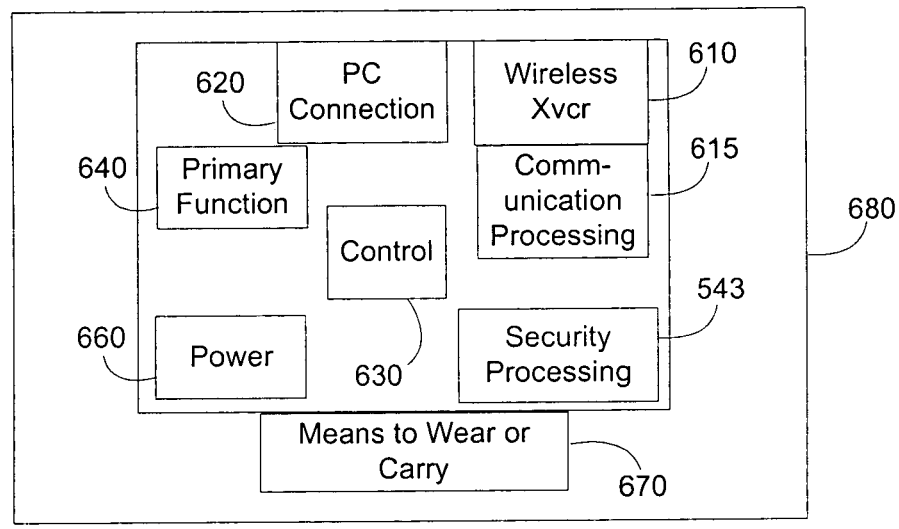
FIG. 6 is a block diagram of an INC.

FIG. 6 shows a block diagram of INC 600. Wireless transceiver 610 may include radio-frequency transmitting circuitry and radio-frequency receiving circuitry. These circuits may, for example, transmit and receive signals at a 2.4 GHz radio frequency. It may also include an antenna. The receiving circuitry may include analog-to-digital conversion circuitry. The transmitting circuitry may include digital-to-analog conversion circuitry. Wireless transceiver 610 may receive data and commands from one or more INCs in the MPN and may send data and commands to one or more INCs in the MPN. If desired, and depending on the type of INC 600, wireless transceiver 610 may include only transmission circuits or only receiving circuits. Communication processing module 615 may include circuitry to process the incoming and outgoing data handled by wireless transceiver 610. It may support low-level and high-level protocols. If desired, different protocol levels may be handled in different modules. The MPN-specific protocol level may operate on top of an industry-standard protocol, such as IEEE 802.15. Communication processing module 615 may also include a log of other INCs that are currently supported within the MPN. It may also include a table of standard INC device types, manufacturers, and capabilities. Extensions to these tables may be downloaded using wireless transceiver 610.

PC connection 620 may provide a connector for a cable that is used to connect INC 600 to a personal computer. It may be, for example, a USB (universal serial bus) connector, allowing the user to connect the INC to a USB port on the PC. The connection may alternatively be any type of wired or wireless connection, such as a serial port, an infrared connection, or any other suitable type of connection. If desired, wireless transceiver 610 may be used to communicate with a radio frequency port on a personal computer. If desired, some INCs may not have PC connection 620.

Control circuitry 630 may include various control functions. For example, it may include processing capabilities and memory or any suitable type. It may also communicate with, and route information between, other modules in the INC, such as wireless receiver 610, communication processing module 615, PC connection 620, primary function 640, security-processing circuitry 543, and power module 660.

Primary function 640 includes circuitry to supply the function that the INC provides to the MPN and to the user. This may include an input function (such as a heart rate or other metabolic sensor, global positioning system receiver or other speed/distance/location sensor, microphone, still or motion digital camera, or user input device), output function (such as a device controller, display device, or audio output), communication device (such as a mobile telephone), processing device, memory device, or any other suitable function. If desired, INC 600 may include multiple such functions.

Security processing circuitry 543 may provide authentication of incoming and outgoing messages and theft protection, as described previously with respect to FIG. 5. Power module 660 provides electrical power for INC 600, and is described more fully with respect to FIG. 7. Means to wear or carry 670 may provide an attachment or other physical means by which the user can wear or carry INC 600. This may include a wristband, a waistband, a headband, a clip, a hook and loop type fastener, or any other appropriate attachment means. It may include the means to wear INC 600 directly on the user's body, or to attach INC 600 to an item of clothing worn by the user. If desired, means to wear or carry 670 may be omitted, if INC 600 is intended, for example, to be carried in a purse or pocket.

Packaging 680 provides for the external appearance and physical characteristics of INC 600. Packaging 680 may provide for protection from the environment. For example, INC 600 may be water resistant, waterproof, shock resistant, drop resistant, radiation hardened, jostle-resistant (e.g., able to be carried in a purse or pocket without interfering with its functions), high or low temperature resistant, or otherwise designed to function well in less than ideal conditions. INC 600 may be designed to be able to be seen easily in various conditions (such as low ambient light, low contrast, etc.), or it may be designed to be difficult to see or to blend in with its background. Packaging 680 may also provide for the aesthetic appearance of INC 600. For example, it may incorporate specific designs, patterns, colors, materials, textures, weight or weight-distribution, etc. It may provide for a specific density (for example, so that INC 600 will float in water or sink in water.) It may provide for ergonomic use of INC 600, for example, making it easy to hold, to view, to operate, or otherwise use.

Figure 7:
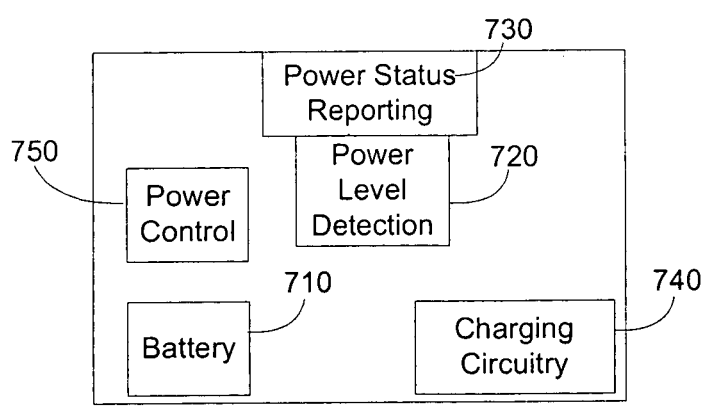
FIG. 7 is a block diagram of the power module of an INC.

FIG. 7 shows more detail of power module 660. Power module 660 may include battery 710. Battery 710 may be replaceable, or it may be hardwired into INC 600. If it is hardwired, it may preferably be rechargeable. Alternatively, it may be designed for long-life under typical use. If battery 710 is replaceable, it may also be rechargeable. Power level detection circuitry 720 may detect the voltage or power level generated by battery 710. It may predict the amount of time remaining or estimate the percentage of battery life remaining. Power status reporting module 730 may report the time or percentage of battery life remaining. If desired, INC 600 may have a user output device, such as a display or audio output, which can be used to report the battery status or alert the user when battery life is low. If desired, the battery status can be sent by power status reporting module 730 to another INC to be reported, using wireless transceiver 610. If desired, the battery status can be sent by power status reporting module 730 to a personal computer to be reported, using PC connection 620. If desired, power module 660 may maintain in memory (for example memory included in control circuitry 630) a log of battery status over time, which can be reported to the user by any appropriate means.

If desired, power module 660 may include charging circuitry 740, to charge battery 710 in place. For example, charging circuitry 740 may include a solar powered charging circuit. If desired, charging circuitry 740 may include circuitry to charge battery 710 using electric power received on PC connection 620. For example, if PC connection 620 is a USB connection, power from the USB connection may be routed to power module 660 to charge battery 710 while INC 600 is connected to a personal computer. If desired, other charging means may be included. For example, charging circuitry 740 may receive power from a docking cradle into which INC 600 may be inserted. If desired, such a docking cradle may also provide PC connection 620.

Power control module 750 may control various power functions. For example, when power level detection circuitry 720 reports that the battery is near the end of its life, power control module 750 may initiate a graceful shutdown of INC 600. This may include storing of interim data values, notifying other INCs in the MPN, and any other suitable actions prior to removing power from INC 600. Power control module 750 may also include a time-based sleep function. After a defined period of inactivity, power control module 750 may place INC 600 into a low-power consumption mode, by turning off some or all functions of INC 600. Power control module 750 may also support a global power-off and global power-on feature. In this feature, the user turns off a single INC, which sends commands to all other INCs in the MPN, directing them to turn themselves off (go into a low-power consumption mode). When the user turns back on the single INC, it sends commands to the other INCs directing them to resume normal operations.

Figure 8:
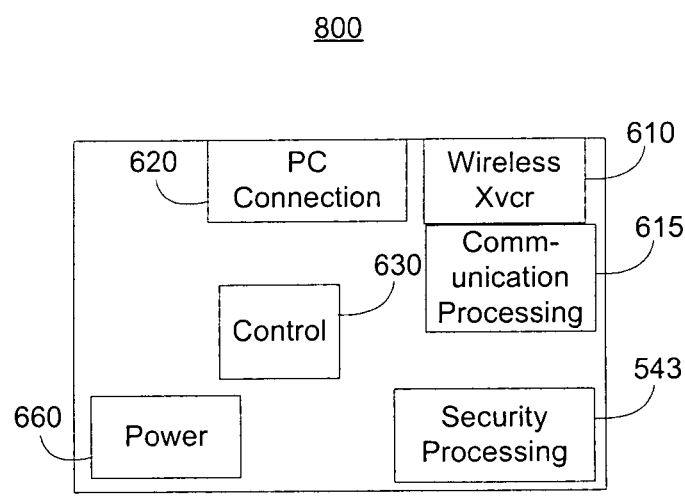
FIG. 8 is a block diagram of an application-specific integrated circuit that may be used within an INC.

If desired, several of the functions of the INC may be integrated into one or more application-specific integrated circuits (ASICs). This may simplify the design and manufacture of different types of INCs, by providing a drop-in module that provides many of the common functions. It may also reduce the cost of each INC, and may also provide for reduced size and power consumption. It may also help ensure consistency in certain features of the INCs. FIG. 8 shows an example of how several functions may be integrated into a single ASIC 800. In this example, ASIC 800 includes wireless transceiver 610, communication processing module 615, PC connection 620, control module 630, security-processing circuitry 543, and power module 660. If desired, ASIC 800 may include only portions of some of these modules. Any suitable arrangement of modules into one or more ASICs may be used, but preferably each ASIC should be designed to be usable in multiple types of INCs.

Figure 9:
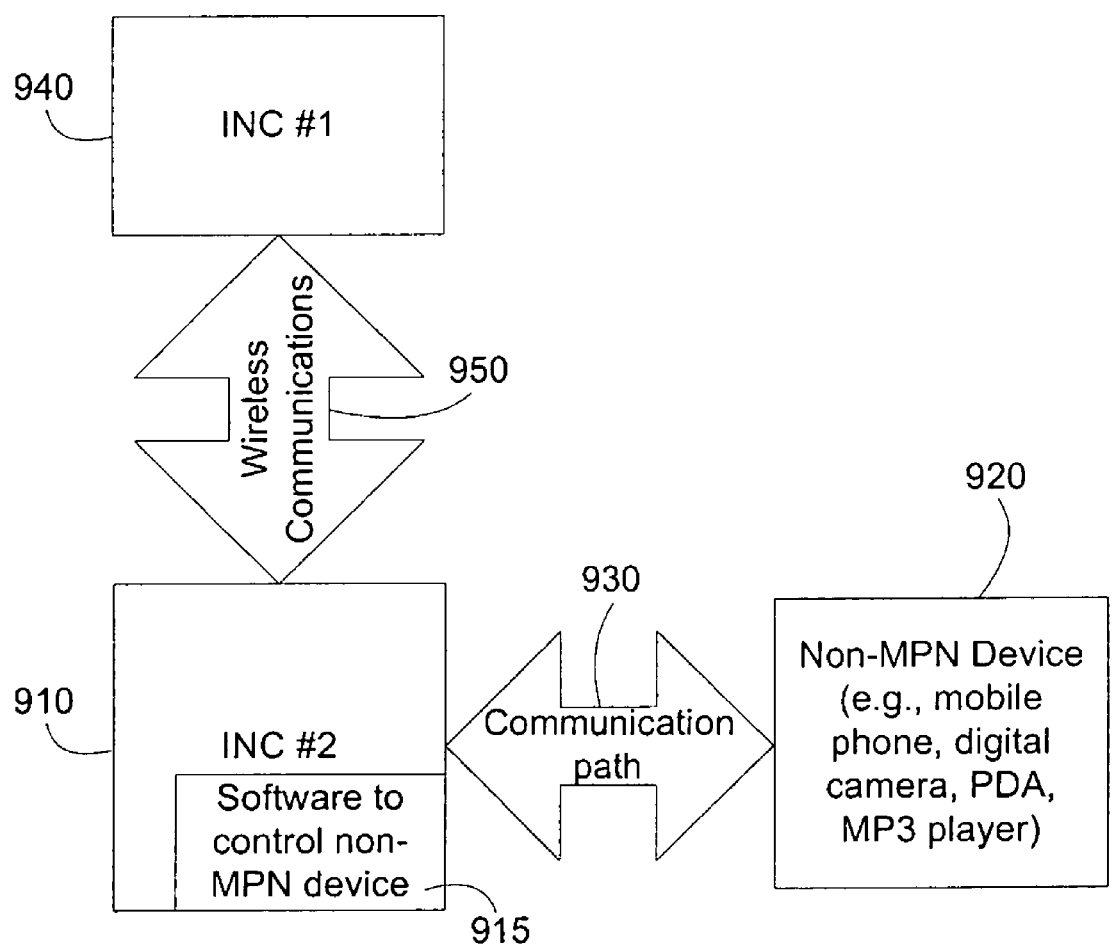
FIG. 9 is a block diagram of an MPN with an INC that has a hard-wired connection to a non-MPN device.

Some users may wish to integrate existing, non-MPN devices into an MPN. For example, a user may have an existing mobile telephone, an existing personal digital assistant (PDA), an existing MP3 player, an existing digital camera, or any other suitable personal electronic device. FIG. 9 shows a block diagram of MPN 900 that integrates an existing non-MPN device 920.

INC 910 provides an interface to non-MPN device 920. INC 910 includes software 915, which may be downloaded from a personal computer. Software 915 is configured to control and access the functions of non-MPN device 920. If desired, INC 910 may also provide any other suitable function or functions. INC 910 accesses non-MPN device 920 over communication path 930. Communication path 930 may be, for example, a USB connection, a mobile phone accessory port, a PDA synchronization port, an infrared port, or any other suitable type of connection. INC 910 makes the functions and features of non-MPN device 920 available to other INCs in the MPN, such as INC 940, over wireless communication path 950. In effect, non-MPN device 920 can be treated as an INC by the other INCs in the MPN.

Figure 10A:
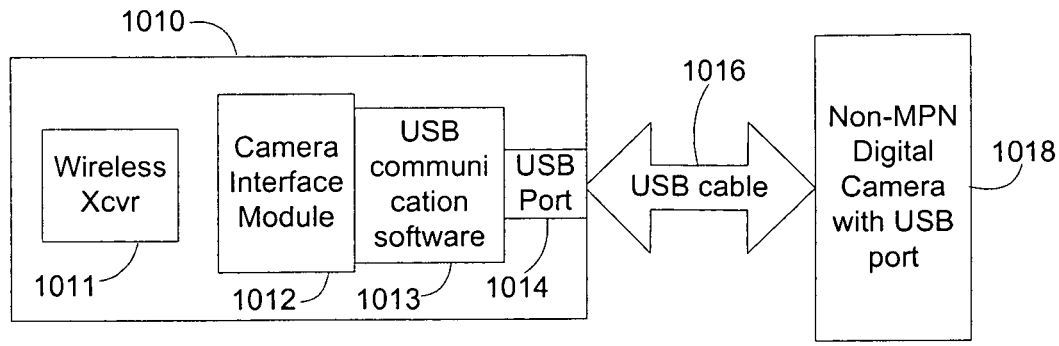
FIGS. 10A through 10E are block diagrams of INCs that interface with non-MPN devices.

FIGS. 10A through 10E show block diagrams of example INCs that provide interface to non-MPN devices. FIG. 10A shows INC 1010 that provides an interface to non-MPN digital camera 1018 with a USB port. INC 1010 includes USB port 1014, to which USB cable 1016 may be connected. The other end of USB cable 1016 may be connected to digital camera 1018. If desired, USB cable 1016 may be zero length, i.e. INC 1010 may connect directly to digital camera 1018. INC 1010 includes USB communication software 1013 that provides the USB protocols. If desired, USB port 1014 and USB communication software 1013 may also be used as method of connecting INC 1010 to a personal computer. INC 1010 also includes camera interface module 1012, which may be software that provides function-based access (e.g. via an application program interface, or API) to various camera functions. These functions may include transferring digital photographs from digital camera 1018, clearing memory on digital camera 1018, taking a photograph using digital camera 1018, changing configuration settings on digital camera 1018, or any other suitable functions. INC 1010 also includes wireless transceiver 1011. Using wireless transceiver 1011, one or more (e.g., any) other INC within the MPN can access the camera functions provided by camera interface module 1012.

Figure 10B:
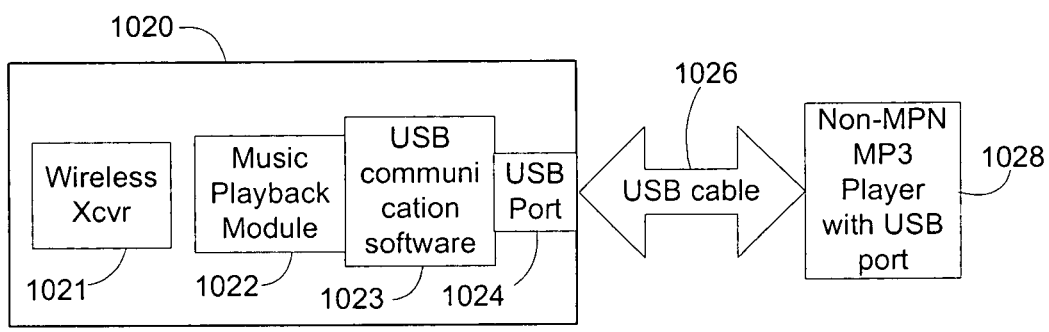

FIG. 10B shows INC 1020 that provides an interface to non-MPN MP3 player 1028 with a USB port. INC 1020 includes USB port 1024, to which USB cable 1026 may be connected. The other end of USB cable 1026 may be connected to MP3 player 1028. If desired, USB cable 1026 may be zero length, i.e. INC 1020 may connect directly to MP3 player 1028. INC 1020 includes USB communication software 1023 that provides the USB protocols. If desired, USB port 1024 and USB communication software 1023 may also be used as method of connecting INC 1020 to a personal computer. INC 1020 also includes music playback module 1022, which may be software that provides function-based access (e.g. via an API) to various MP3 player functions. These functions may include transferring songs to MP3 player 1028, clearing memory on MP3 player 1028, playing back a song or set of songs using MP3 player 1028, changing configuration settings on MP3 player 1028, or any other suitable functions. INC 1020 also includes wireless transceiver 1021. Using wireless transceiver 1021, one or more (e.g., any) other INCs within the MPN can access the MP3 player functions provided by music playback module 1022.

Figure 10C:
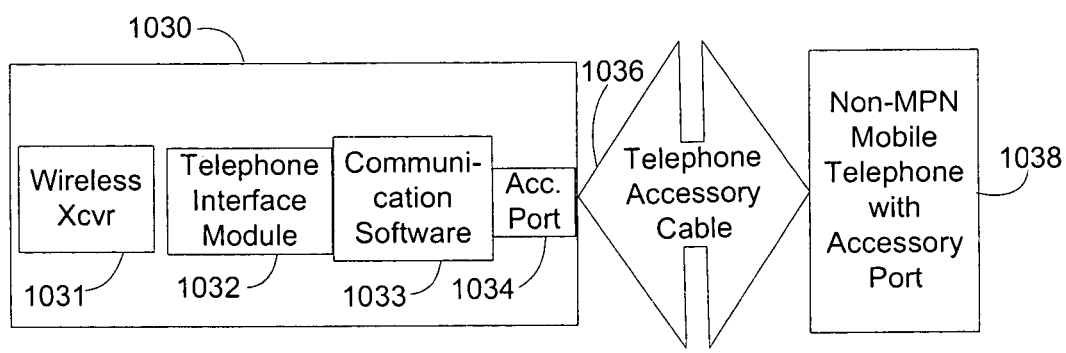

FIG. 10C shows INC 1030 that provides an interface to non-MPN mobile telephone 1038 with an accessory port. INC 1030 includes accessory port 1034, to which telephone accessory cable 1036 may be connected. The other end of telephone accessory cable 1036 may be connected to mobile telephone 1038. If desired, telephone accessory cable 1036 may be zero length, i.e. INC 1030 may connect directly to mobile telephone 1038. INC 1030 includes telephone communication software 1033 that provides the protocols to communicate with mobile telephone 1038. INC 1030 also includes telephone interface module 1032, which may be software that provides function-based access (e.g. via an API) to various mobile telephone functions. These functions may include transferring phone numbers to mobile telephone 1038, making a call on mobile telephone 1038, adjusting the volume on mobile telephone 1038, changing configuration settings on mobile telephone 1038, or any other suitable functions. INC 1030 also includes wireless transceiver 1031. Using wireless transceiver 1031, one or more (e.g., any) other INCs within the MPN can access the mobile telephone functions provided by telephone interface module 1032.

Figure 10D:
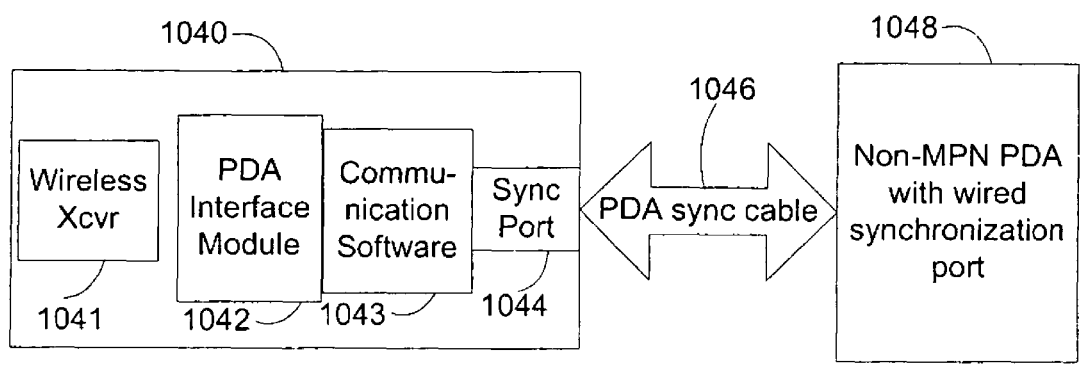

FIG. 10D shows INC 1040 that provides an interface to non-MPN PDA 1048 with a wired synchronization port, for example a serial port or a USB port. INC 1040 includes synchronization port 1044, to which synchronization cable 1046 may be connected. The other end of synchronization cable 1046 may be connected to PDA 1048. If desired, synchronization cable 1046 may be zero length, i.e. INC 1040 may connect directly to PDA 1048. INC 1040 includes PDA communication software 1043 that provides the protocols to communicate with PDA 1048. INC 1040 also includes PDA interface module 1042, which may be software that provides function-based access (e.g. via an API) to various PDA functions. These functions may include transferring contact information to/from PDA 1048, transferring appointment information to/from PDA 1048, using PDA 1048 as an input device for other MPN functions, using PDA 1048 as a display device for any other MPN functions, or any other suitable functions. INC 1040 also includes wireless transceiver 1041. Using wireless transceiver 1041, one or more (e.g., any) other INCs within the MPN can access the PDA functions provided by PDA interface module 1042.

Figure 10E:
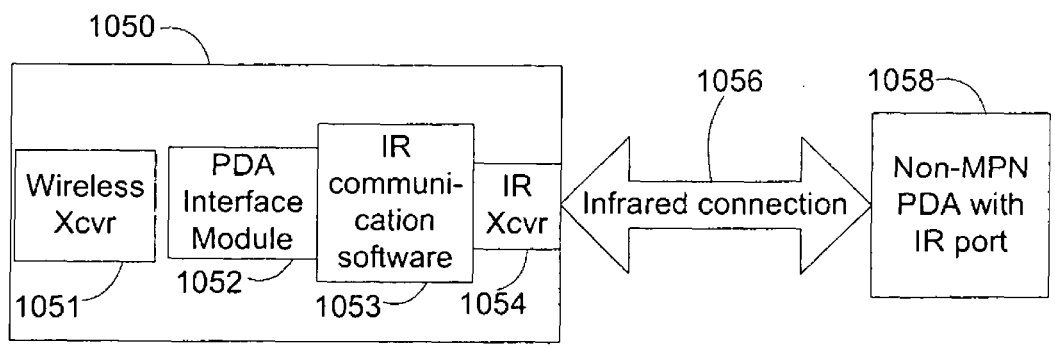

FIG. 10E shows INC 1050 that provides an interface to non-MPN PDA 1058 with an infrared communication port. INC 1050 includes infrared transceiver 1054. A wireless infrared connection 1056 may be made between PDA 1058 and INC 1050, by directing the transceiver on each unit in the direction of the other. INC 1050 includes IR communication software 1053 that provides the protocols to communicate with PDA 1058 over IR communication path 1056. If desired, infrared transceiver 1054 and IR communication software 1053 may also be used as method of connecting INC 1050 to a personal computer. INC 1050 also includes PDA interface module 1052, which may be software that provides function-based access (e.g. via an API) to various PDA functions. These functions may include transferring contact information to/from PDA 1058, transferring appointment information to/from PDA 1058, using PDA 1058 as an input device for other MPN functions, using PDA 1058 as a display device for any other MPN functions, or any other suitable functions. INC 1050 also includes wireless transceiver 1051. Using wireless transceiver 1051, one or more (e.g., any) other INCs within the MPN can access the PDA functions provided by PDA interface module 1052.

Figure 11:
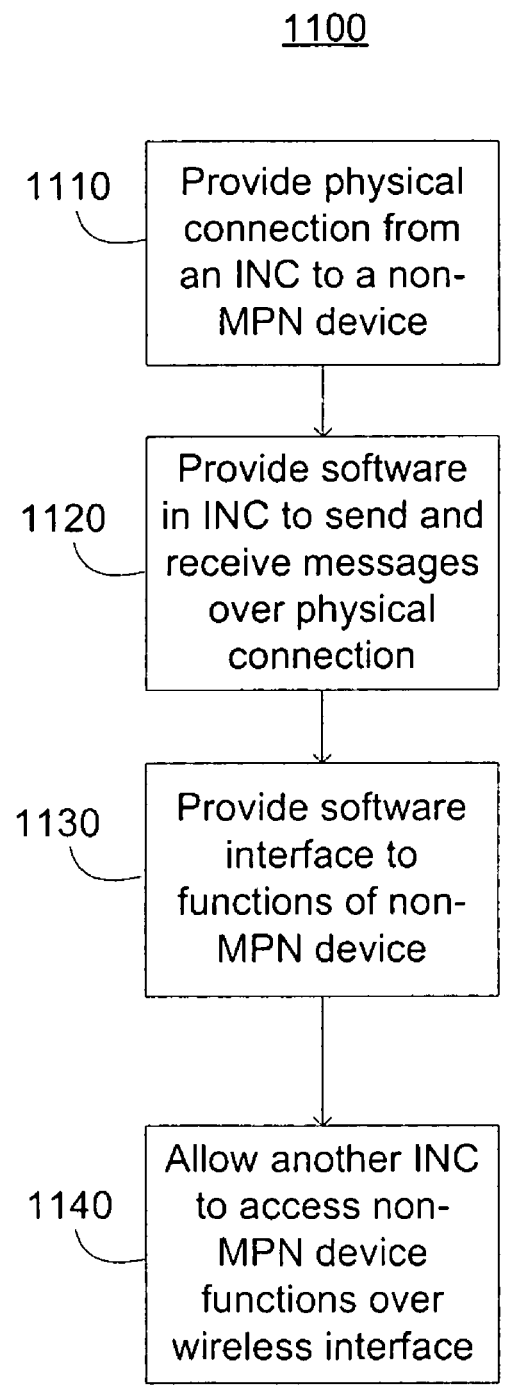
FIG. 11 is a flowchart of an illustrative process for providing an interface to a non-MPN device within an MPN.

FIG. 11 shows flowchart 1100 of illustrative steps to integrate a non-MPN device into an MPN. All steps in flowchart 1100 are optional and may be performed in any suitable order. In step 1110, a physical connection is provided between an INC in an MPN and a non-MPN device. The physical connection preferably makes use of a connection type already supported by the non-MPN device. The physical connection may be wired or wireless. For example, it may be USB, serial port, IR, accessory port, synchronization port, or any other suitable existing connection. If desired, the physical connection may be the same as the wireless connection used to communicate between INCs in the MPN, if the non-MPN device supports wireless communications, for example, if it is a Bluetooth device. In step 1120, software is provided in the INC to communicate using the physical connection to the non-MPN device. This software may provide one or more protocol layers. It may include, for example, USB drivers, IR drivers, or drivers to interface with a proprietary accessory port or synchronization port. If desired, the physical connection provided in step 1110 and/or the communication software provided in step 1120 may also be used for other purposes by the INC, such as to communicate with a personal computer.

In step 1130, a software interface may be provided in the INC to access functions of the non-MPN device. For example, an API may provide a message-based or function-based interface to any suitable subset of functions implemented in the non-MPN device. If desired, the functions provided need not map one-to-one to functions provided by the non-MPN device. In step 1140, other INCs in the MPN are allowed to access the functions of the non-MPN device. For example, a command may be sent by another INC and received by the interfacing INC. The received command may map onto a function from the device API. The interfacing INC may send one or more commands and/or data to the non-MPN device, which may in turn return results and/or data. The interfacing INC may then return the appropriate results, which may be derived from the results provided from the non-MPN device, to the other INC.

Figure 12:
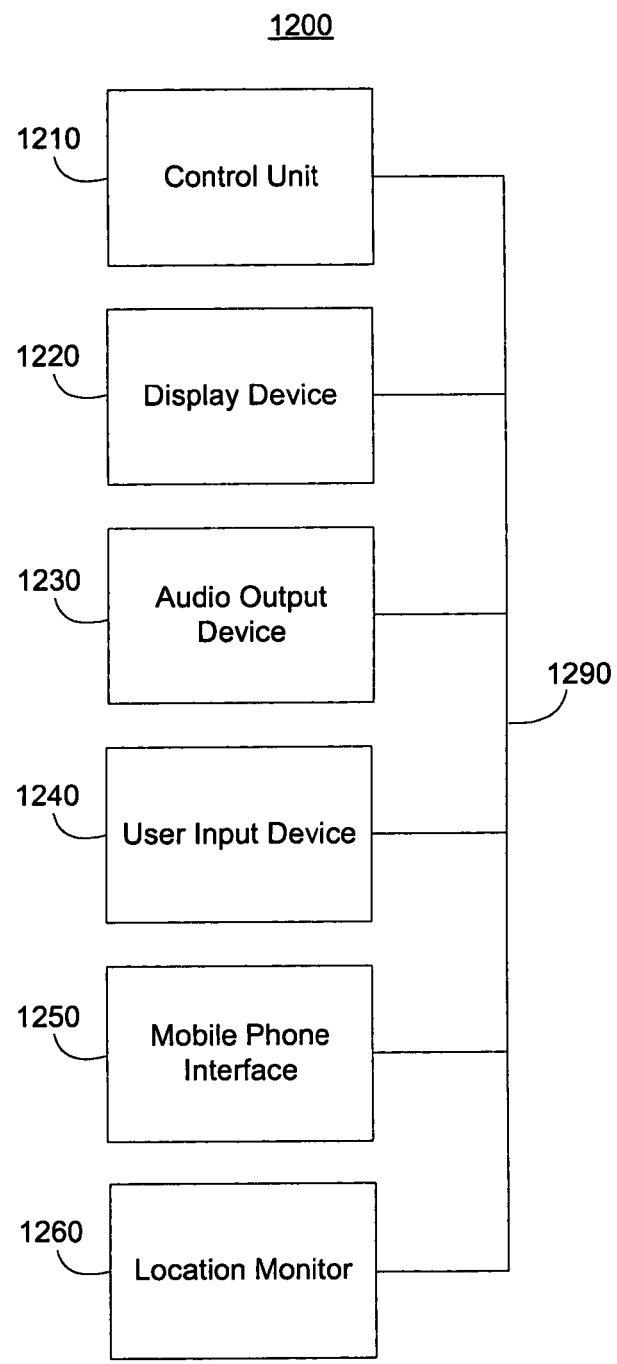
FIGS. 12 and 13 are block diagrams of illustrative MPNs.
Figure 13:
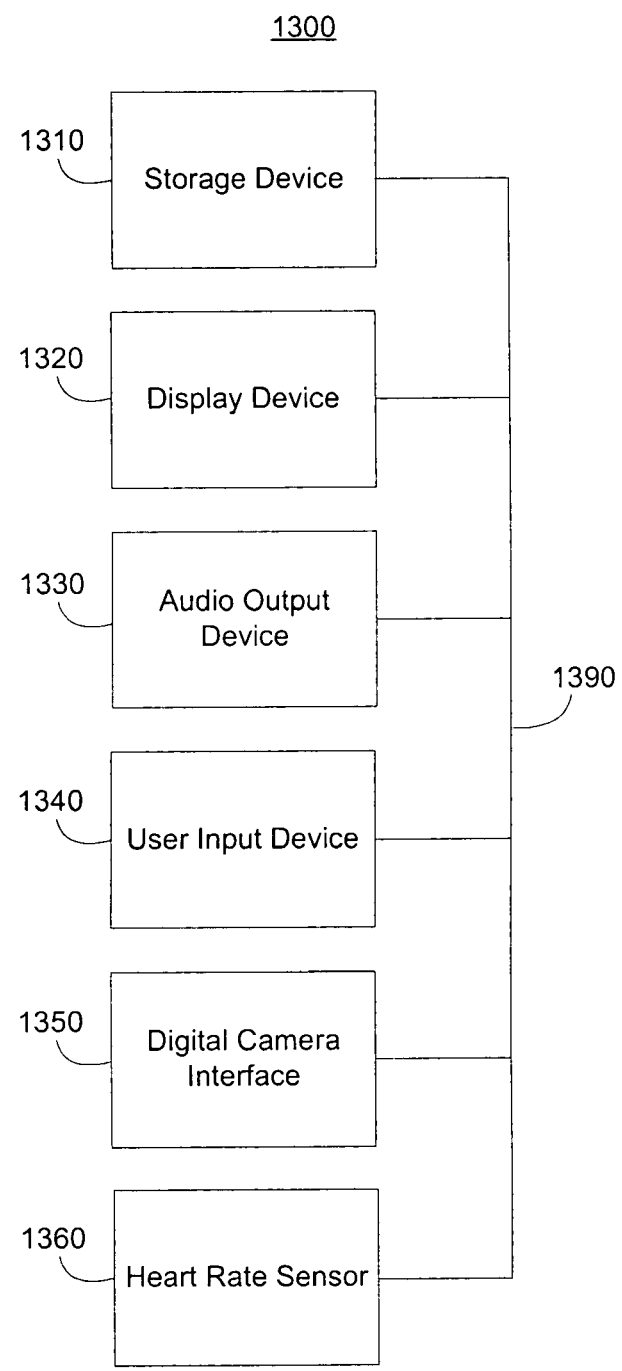

Every MPN is unique, and has a unique set of capabilities, depending on the needs of the individual user. The user can modify the MPN at any time depending on the needs of the day or hour, or the specific occasion or event. It is simple to add or remove one or more INCs at any time. FIGS. 12 and 13 show block diagrams of example individual MPNs.

FIG. 12 shows a block diagram of example MPN 1200. MPN 1200 includes control unit 1210. Control unit 1210 can be considered the general-purpose processor for controlling the functions of MPN 1200. It includes a microprocessor and memory. The memory can be used for downloading software modules to control the other INCs and to perform other specific functions. It can also be used for collecting data from the other INCs. Memory can be of any type or combination of types, such as RAM, hard disk, CD-ROM, mini-disk, or flash memory, and may be permanent or removable. Control unit 1210 may be worn on the user's waist, worn on a wristband, carried in a pocket or purse, or carried or worn in any other suitable manner. If desired, functions of control unit 1210 may be combined into a single INC with other functions, such as display and user input functions.

Display device 1220 may typically be a general-purpose graphical or alphanumeric display, such as a liquid crystal display, or LCD. It may, for example, be worn on the wrist. Audio output device 1230 may include one or more speakers to output music, audio status information, generated speech, or any other audio content. It may also include digital-to-analog converters and amplifiers to generate an appropriate audio signal to output. It may be worn in the form of a set of headphones, a single ear bud, a speaker that is attached to a hat or headband, or any other suitable form. It may also be in the form of a speaker embedded into another INC.

User input device 1240 may include one or more of any suitable type of user input. This may include one or more buttons, a microphone with speech recognition, pen-based input, a keyboard, or any other appropriate portable user input device. User input device 1240 may be worn on the hand or wrist, attached to a set of headphones, worn at the waist, or worn or carried in any other suitable manner. User input controls, such as buttons, may also be incorporated into any other INC, such as a display device or control unit.

Mobile telephone interface 1250 may make the functions of the user's non-MPN mobile telephone available to the other INCs in MPN 1200, as described above with respect to FIG. 10C. Mobile telephone interface 1250 may be designed to be worn on the waist or carried in a pocket or purse, or otherwise carried or worn. The functions of mobile telephone interface 1250 may also be included in another INC, such as a control unit.

Location monitor 1260 may include a global positioning system (GPS) receiver and antenna, to provide current location and speed information to the other INCs in MPN 1200. It may be designed to be worn on an armband or a waistband, or otherwise to be worn or carried. If desired, the GPS antenna may be separate from the GPS receiver. If desired, the functions of location monitor 1260 may be integrated into another INC, such as control unit 1210, or mobile telephone interface 1250.

The INCs in MPN 1200 communicate over wireless communication path 1290. This includes sending commands, responses, data, information, audio to be output, information to be displayed, user input commands, mobile telephone commands, position and speed information, and any other suitable messages.

FIG. 13 shows a block diagram of another MPN 1300. MPN 1300 is different from MPN 1200 in that it does not include a control unit. Instead, control is distributed among the INCs in MPN 1300. Each INC provides its functions to the other INCs independently. Display device 1320, audio output device 1330, and user input device 1340 are similar to INCs 1220, 1230, and 1240, respectively, as described previously in conjunction with FIG. 12.

Storage device 1310 includes memory that can be used by the other INCs in MPN 1300. Memory can be of any suitable form, such as RAM, flash memory, mini-disk, etc., and may be permanent or removable. Data, such as digital music files, can be loaded into storage device 1310 from a personal computer. Data may be sent from storage device 1310 to other INCs, such as audio output device 1330. In that example, music may be generated from the music files and output using audio output device 1330. Data may be sent by other INCs, such as digital camera interface 1350 and heart rate sensor 1360 and stored by storage device 1310. The data collected by storage device 1310 may later be sent to a personal computer. Storage device 1310 may be worn on the user's waist, worn on a wristband, carried in a pocket or purse, or carried or worn in any other suitable manner. If desired, functions of storage device 1310 may be combined into a single INC with other functions, such as display and user input functions.

Digital camera interface 1350 may make the functions of the user's non-MPN digital camera available to the other INCs in MPN 1300, as described above with respect to FIG. 10A. Digital camera interface 1350 may be designed to be worn on the waist or carried in a pocket or purse, or otherwise carried or worn. The functions of digital camera interface 1250 may also be included in another INC, such as a storage device.

Heart rate sensor 1360 may include a sensor to measure heartbeats. It may be designed to be worn on a chest strap.

The INCs in MPN 1300 communicate over wireless communication path 1390. This includes sending commands, responses, data, information, music and other audio to be output, information to be displayed, user input commands, digital camera commands, digital images, heart rate data, and any other suitable messages.

INC 1200 and INC 1300 are shown purely by way of illustration. A user may configure any suitable combination of INCs into an MPN. A user may also change which INCs are included in an MPN at different times, based on specific circumstances, needs, mood, or any other factors.

A user can purchase MPN components in any suitable package from any manufacturer. If desired, INCs from different manufacturers can be mixed within a single MPN. If desired, an INC from one manufacturer can be replaced by an INC from another manufacturer.

Figure 14:
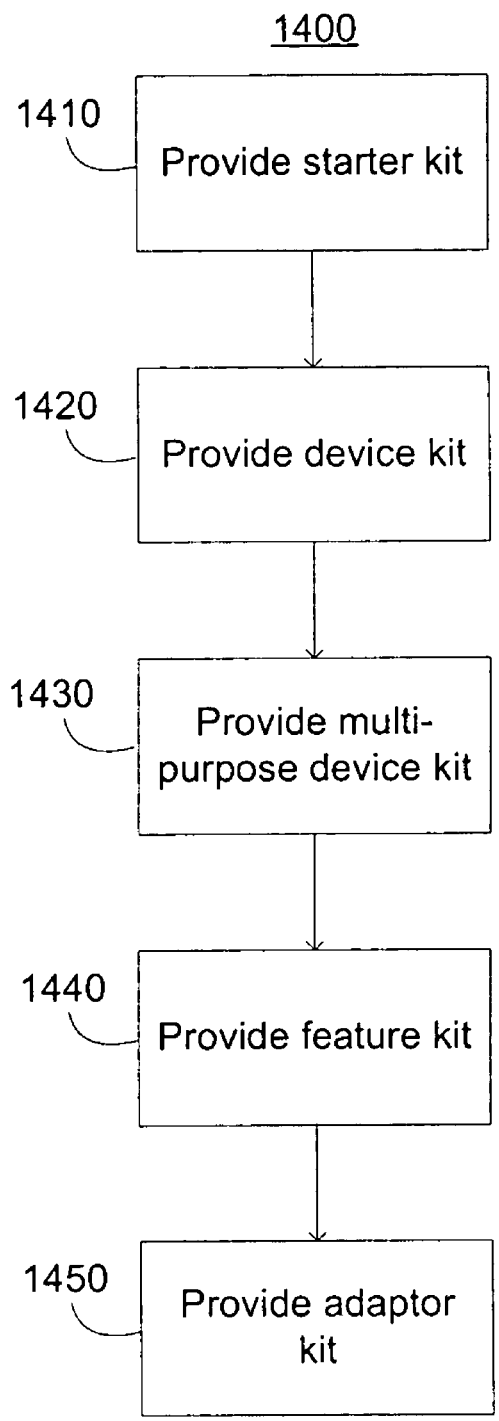
FIG. 14 is a flowchart of an illustrative process for providing various MPN product packages.

FIG. 14 shows flowchart 1400 of steps that may be performed to provide various packages of MPN components and related product items. Some of the steps in flowchart 1400 are optional and may be performed in any suitable order. In step 1410, a starter kit may be provided. The starter kit may include an application that can be loaded onto a PC to control and configure the MPN. It may include a security lock value, as discussed above in conjunction with FIG. 3. It may include one or more basic INCs, such as a control unit, a display device, etc. It may include a PC connection cable or docking station. It may include a link to a website to find updated plug-ins for the PC control application, device drivers, device lists, etc. It may include one or more user instruction manuals. It may also include coupons for other MPN products offered by the same manufacturer. It may include any other suitable items.

In step 1420, a device kit may be offered. This kit includes a specific INC. It may also include a plug-in for the PC application to configure the INC, a device driver to be downloaded to the device or to a control unit, a PC connection cable or docking station, a link to a website for updates, one or more instruction manuals, or any other suitable items.

In step 1430, a multi-purpose device kit may be provided. This may be similar to the device kit provided in step 1420, with the addition that the single INC may provide multiple features.

In step 1440, a feature kit may be provided. The feature kit includes all items necessary to add a specific feature to an MPN. This may include one or more INCs (if the feature cannot be implemented using existing INCs). It may include a plug-in for the PC application. It may include one or more device drivers to be downloaded into INCs in the MPN. It may include one or more cables. It may also include a link to a website for updates, an instruction manual, and any other suitable items.

In step 1450, an adaptor kit may be offered. The adaptor kit may include an INC that is configured to communicate with a non-MPN device, as described above in conjunction with FIG. 11. The kit may include one or more adaptor cables (each cable configured for a specific subset of non-MPN devices), a plug-in for the PC application, device drivers, a website link for updates, an instruction manual, and any other suitable items.

Each MPN can perform many functions, depending on the components included by its user and depending on the software and configuration parameters loaded. Some of the most common functions may include time keeping functions (such as current time, stop watch functions, etc.), personal organizer functions (such as contact management and appointment notification), music playback, and games.

If desired, an INC in one MPN can communicate with an INC in another MPN, when the users are in close proximity. When a message is sent from an INC, it may be tagged with an identification of the MPN in which it originated. An INC can use this information to generate a message that is targeted for an INC in the other MPN. This can be used, for example, to allow two or more users to play a multi-user game or participate in any other type of multi-user competition. Each user may use his or her own input device, display, and audio output, and information related to the game or competition may be sent in messages between the INCs in the MPNs.

MPN users can also exchange other types of data. For example, a user of one MPN can send software, which may be control software for an INC in the MPN, to the user of another MPN. A user of one MPN can send personal information, such as contact information, to a user of another MPN. A user of one MPN can send media files, such as digital music files and digital photographs, to a user of another MPN.

Another example of information exchange between MPNs is between musicians. A musician may have an MPN with INCs designed to support music-related functions. For example, the musician may have one or more INCs that include microphones, one or more INCs that include speakers, an INC that has memory to store music (e.g., as sheet music, as digital audio files, or in any other suitable format), an INC that can convert music from one format (e.g., Midi) to another (e.g., MP3) for output, an INC to perform audio processing and other special effects, an INC to mix multiple inputs, an INC to display sheet music, and any other suitable functions. If desired, an INC can support multiple music-related functions. If desired, the musician's MPN may include INCs that are used for non-music-related functions.

Figure 15:
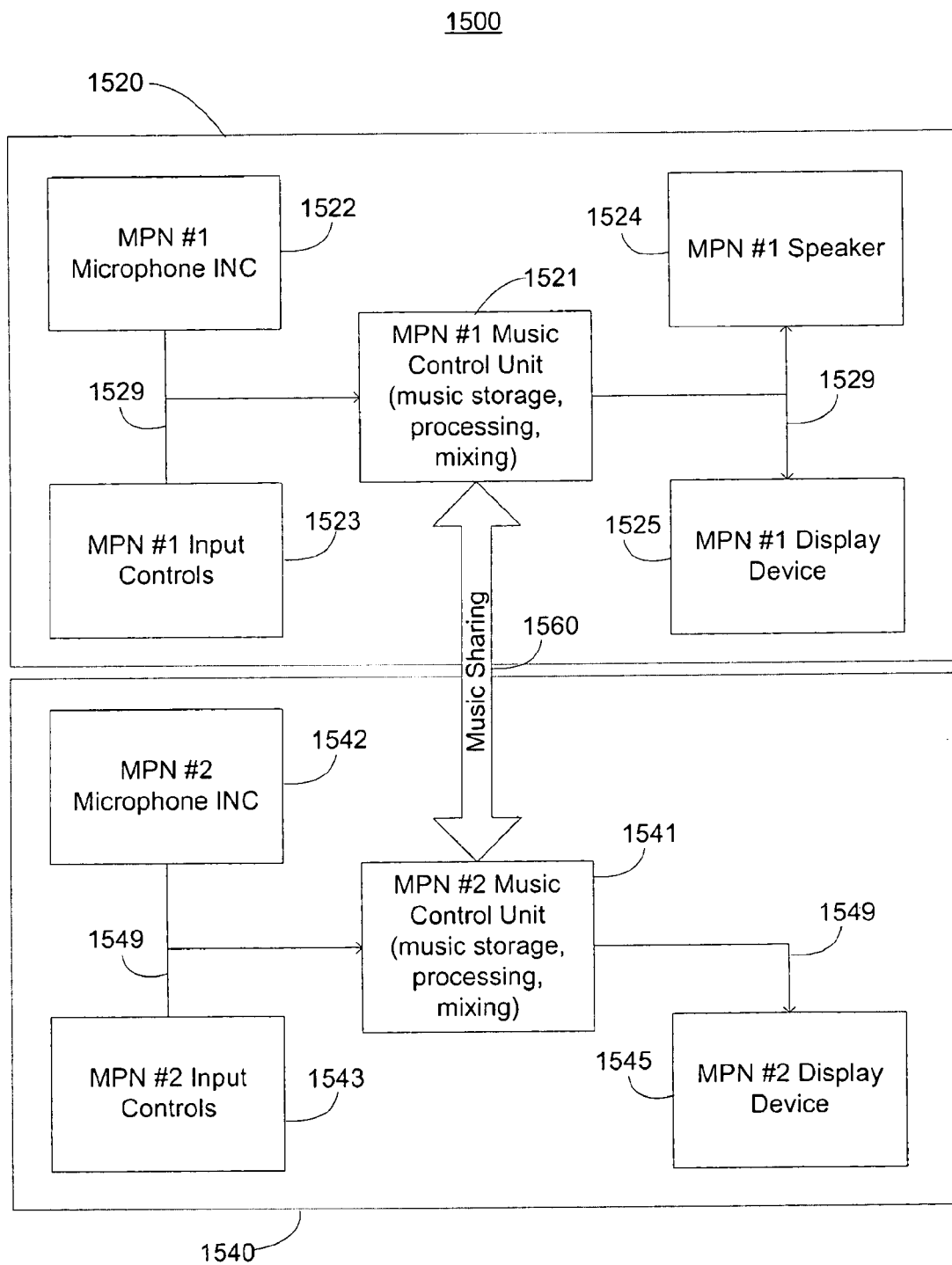
FIG. 15 is a block diagram of an illustrative music collaboration system.

FIG. 15 shows a block diagram of two MPNs that may be used by two musicians to collaborate in music-related activities. Only two MPNs are shown for simplicity, although more than two musicians can easily use their MPNs to collaborate in music. The INCs shown are illustrative, and may vary from MPN to MPN.

Music collaboration system 1500 includes MPN 1520 and MPN 1540. The components of each MPN are associated with a single user, and may be worn, carried, or in close proximity to that user. When the users of the two MPNs are in close proximity to each other, the INCs in their MPNs may send messages and music collaboration is made possible.

MPN 1520 includes INC 1521, which may be a control unit. Control unit 1521 may include a processor for performing music-related processing, and memory for storing music-related data. For example, it may store sheet music files, Midi files, MP3 files, or any other type of music files. It may perform music-related functions, such as special effects, gain control, format conversion, mixing of multiple inputs, or any other suitable music or audio processing functions. INC 1522 may include a microphone. If desired, MPN 1520 may include multiple microphone INCs, or other INCs to provide for input of audio signals, for example directly from musical instruments. INC 1523 may include input controls. These may include, for example, buttons, a computer-type keyboard, a music-type keyboard, a touch screen interface, knob or level type analog inputs, or any other suitable type of input device. Multiple input devices may be included. INC 1524 may include a speaker and amplifier. If desired, multiple speaker INCs may be provided. INC 1525 may be a display device.

The second musician's MPN 1540 may be similar, and the selection of INCs may vary. In this example, MPN 1540 includes control unit 1541, microphone 1542, input controls 1543, and display device 1545, similar to INC 1521, INC 1542, INC 1543, and INC 1545, respectively. In this example, the second MPN does not include a speaker.

Some of the features of the music collaboration system include messages sent between the individual MPNs over wireless communication path 1560 to coordinate the timing and playing of a single piece of music. The displays of each MPN can show the same piece of music, or the relevant part of the same piece of music. Timing signals, such a metronome pulses, can be sent to an audio or display device for each musician. Timing signals may also be displayed directly on the sheet music. Multiple audio inputs, received by INCs in multiple MPNs, can be mixed and stored by an INC in one of the MPNs, as well as played on speakers that are part of one or more of the MPNs. The recorded music can later be uploaded to a PC or other music processing system for later processing. The music generated by the multiple musicians can be processed within any of the MPNs.

Figure 16:
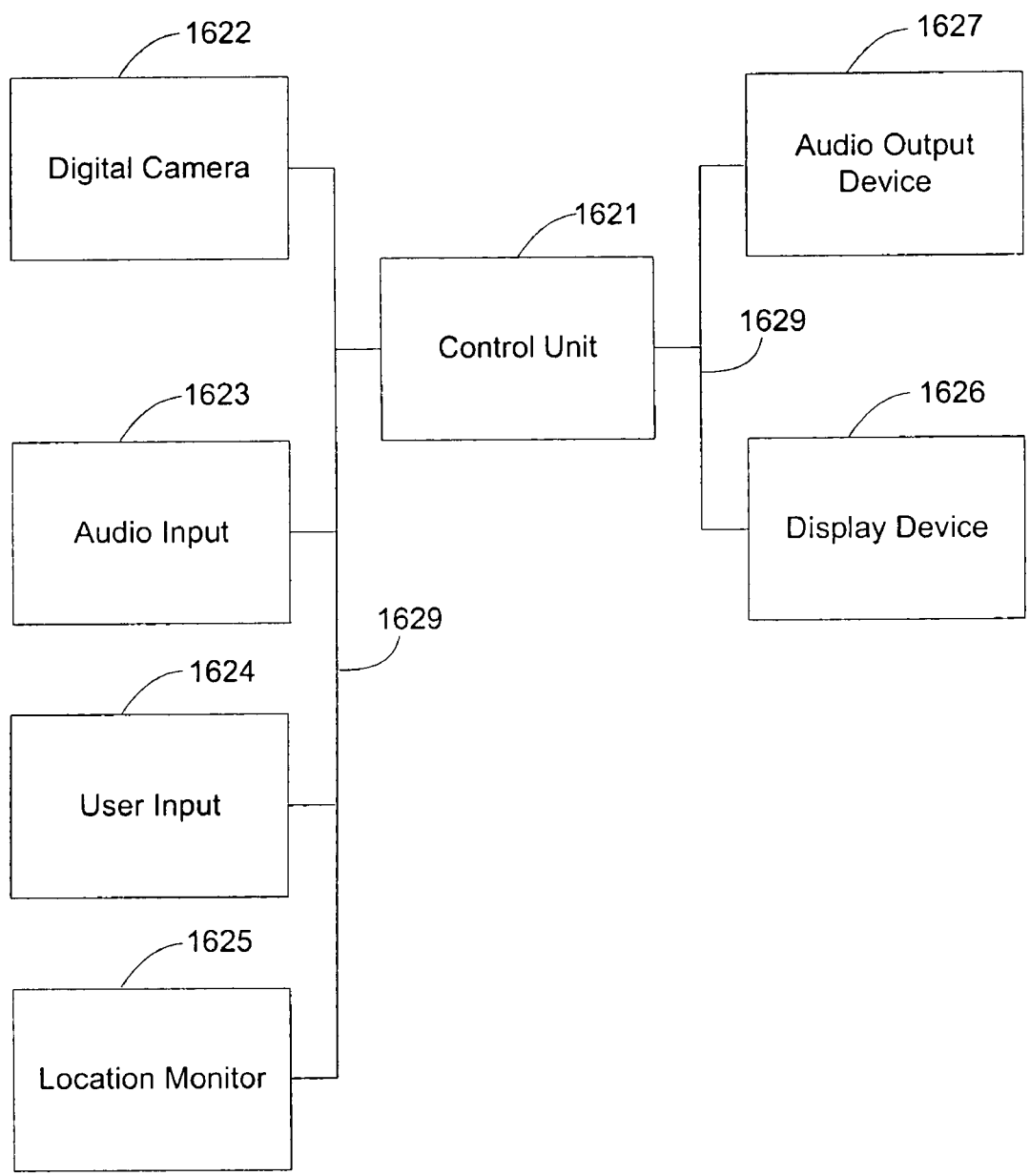
FIG. 16 is a block diagram of an illustrative wildlife recognition and logging system.

FIG. 16 shows a block diagram of another illustrative MPN configuration 1600. MPN 1600 may be configured to provide mobile wildlife recognition and logging. Note that MPN 1600 may also be used for other purposes, such as mobile recognition of other objects, as an electronic journal, or any other suitable purpose. INC 1621 is a control unit. It may include a processor, memory, and a clock. INC 1622 is a digital camera. It may alternatively be an INC configured to interface with a non-MPN digital camera, as described above in conjunction with FIG. 10A. INC 1623 is an audio input device. It may includes a microphone and an analog-to-digital converter. It may be used for capture of external audio samples, as well as for input of user voice commands. INC 1624 may be a user input device. If desired, INC 1623 may be used as a user input device. If desired, user input may be provided with any suitable combination of keyboard, buttons, pen-based input, touch screen, or any suitable other device. If desired, multiple user input INCs may be included INC 1625 may be a location monitor, and may include a GPS receiver and antenna. INC 1626 may be a display device. INC 1627 may be an audio output device. The INCs in MPN 1600 communicate over wireless communication path 1629.

The configuration shown in FIG. 16 is merely illustrative. Other INCs may be included if desired. Some INCs may be omitted. If desired, functions of multiple INCs may be combined into a single device.

Figure 17:
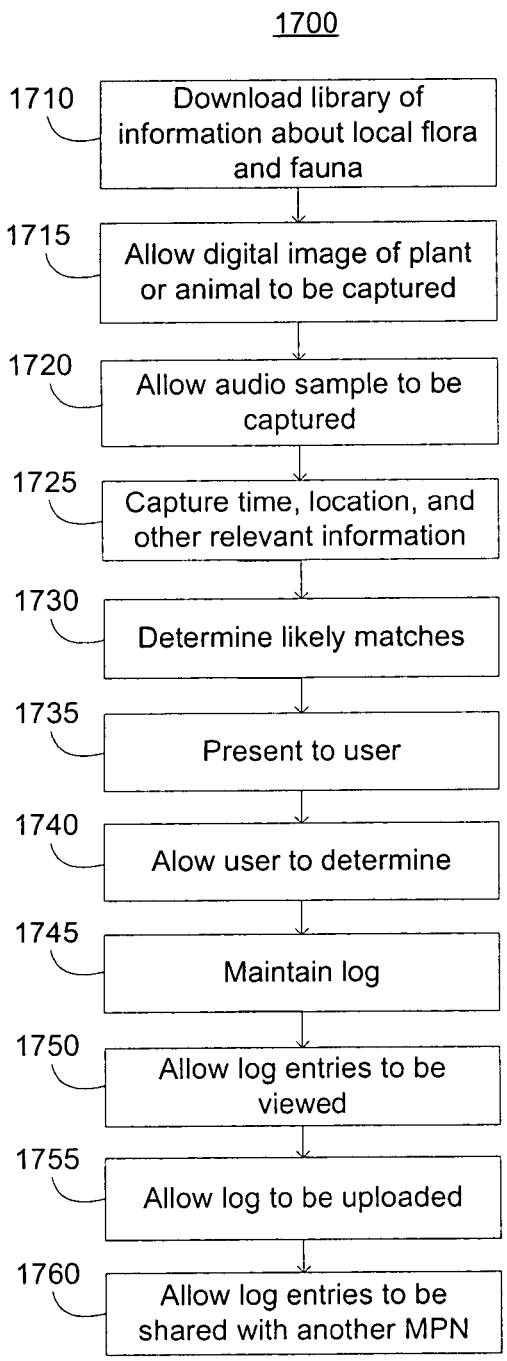
FIG. 17 is a flowchart of an illustrative process for providing a mobile wildlife recognition and logging system.

FIG. 17 shows illustrative flowchart 1700 of a process that may be used to provide mobile wildlife recognition and logging of individual sightings. All steps in flowchart 1700 are optional and may be performed in any suitable order. In step 1710, a library of information about local flora and/or fauna may be downloaded into memory on one of the INCs, such as control unit 1621. The library may be downloaded from a personal computer. The library may have been loaded on the personal computer over the Internet, or using a removable storage device such as a CD-ROM or DVD-ROM. If desired, INC 1621 may be configured to use a removable storage device, such as a flash memory card or mini-disk, and the library may be loaded onto the removable storage device. The library may be related to flora and fauna that may be found in a particular region that the user may be planning to visit. It may include digital images, audio samples of animal calls, information about habits and territories, text descriptions, and any other suitable information.

In step 1715, the user may be allowed to capture an image (or multiple images) at a sighting, which may be of an animal or plant or other suitable object. The user may use digital camera INC 1622, and the captured image may be stored in memory on one of the INCs, such as control unit 1621. If desired, the user may also capture one or more audio samples in step 1720. The audio sample may be, for example, the call of the animal of which the image was capture. Other relevant information may also be captured in step 1725, and stored into memory in control unit 1621. This may include logging the current day and time, which may be done using the clock which is part of control unit 1621. It may also include the current location, which may be captured by location monitor 1625. Any other suitable information may also be captured and stored into memory in control unit 1621. This may include, for example, the current weather conditions. It may also include information entered by the user on user input device 1624. For example, the user may enter notes about the activities of the animal, the environment, or any other notes of interest.

In step 1730, the system may determine likely matches between the captured image and the items in the downloaded library. This may be done by comparing the captured image to the images in the library, comparing the captured audio sample to the audio samples in the library, comparing the captured time and location to information about the habits of the items in the library, or using any other comparisons. Any of these comparisons may also be done in combination. The processor in control unit 1621 may perform the comparisons. Based on the results of these comparisons, one or more of the most likely matches may be chosen. In step 1735, the most likely matches may be presented to the user. This may include displaying one or more images from the library for each match on display device 1626. It may also include playing audio samples, such as animal calls, from the library on audio output device 1627. Other information related to the matched items from the library may also be presented to the user, for example on display device 1626. In step 1740, the user may be allowed to choose one or more of the likely matches, or to rank the likely matches, or to exclude one or more of the likely matches using user input device 1624.

In step 1745, the system may maintain a log, for example in memory in control unit 1621, of each sighting. Each log entry includes all of the captured images, all of the captured audio samples, the time and location stamp of the sighting, current weather conditions if available, any additional information entered by the user, and the results of the match, including the user determination or ranking. In step 1750, the user may be allowed to view past log entries, including all of the related data, captured images, and captured audio samples. The user may also be able to augment the notes or refine the match. In step 1755, the user may be allowed to upload all of the information from the log to a personal computer. This may include converting the various items of data to suitable formats for viewing and processing on the personal computer. For example, the personal computer may create or augment a database file, with links to image files (e.g., JPEG) and audio files (e.g., MP3). Software on the personal computer may allow the user to view and edit the log. There may also be an Internet interface that allows multiple users to upload log entries and share and compare them. In step 1760, the log entries may be shared between the MPN and another MPN that may have similar features. For example, two naturalists, each with his or her own wildlife recognition and logging system, may swap sighting logs. In this case, each log entry may also be automatically tagged with the identification of the person who made the sighting.

Figure 18:
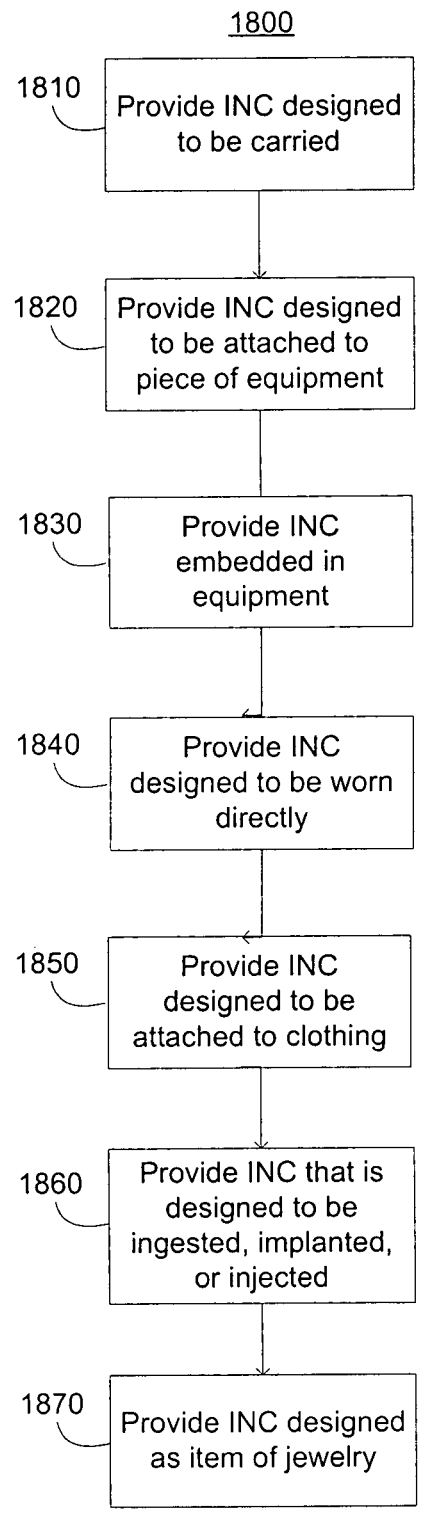
FIG. 18 is a flowchart of an illustrative process for allowing individual network components to be worn or carried.

Each INC is designed to function in close proximity to the user of the MPN. An INC may have means to wear or carry 670, as shown in FIG. 6. There are many examples of how any particular INC can be designed to provide means to wear or carry 670. Illustrative methods for designing INCs to be carried or worn are shown in flowchart 1800 of FIG. 18. All steps in flowchart 1800 are optional and may be performed in any suitable order.

In step 1810, some INCs may be designed to be carried in a pocket or purse. In this case, there may not be a specific means to wear. However, the INC may be designed in a manner so that its functions are not disturbed by jostling that may occur when carried in this manner.

In step 1820, some INCs may be designed to be attached to a piece of equipment that is in close proximity to the user of the MPN. For example, the INC may be attached to a piece of exercise equipment (e.g., a treadmill), to a bicycle, to a car, or to a wheelchair. It may also be mounted on an item of furniture, such as a bed or chair.

In step 1830, some INCs may be embedded into another piece of equipment. For example, an item of medical equipment that may be carried by a doctor or therapist, or may be used by a doctor or therapist, may act as an INC in the doctor's or therapist's MPN, or in the patient's MPN.

In step 1840, some INCs may be designed to be worn directly by the user, or may have attachment means to allow them to be worn directly. For example, an INC may have a wristband or a waistband. Some INCs may be designed to be mounted on a special item of clothing that is worn by the user. For example, an INC may be mounted to a special glove or headband that is designed specifically to facilitate the mounting of INCs.

In step 1850, some INC may be designed to be attached to a user's existing clothing. For example, an INC may be help in place by the fit of an item of clothing, or it may be attached to the clothing using means such as a pin, a hook and loop fastener, or any other suitable means.

In step 1860, some INCs may be designed to be carried internally to the user's body. These INCs may, for example, be injected into the user's blood stream, ingested by the user, or implanted into the user's body.

In step 1870, some INCs may be designed as items of jewelry. As jewelry items, they may mount directly on the body, or they may attach to clothing worn by the user. These jewelry INCs may be designed to look like jewelry, hiding the appearance of being an electronic device, as well as being designed for aesthetic enjoyment. Any of these INCs may include one or more precious, semi-precious, or costume stones, a crafted design, real or imitation precious metals, or any other components to enhance the aesthetic value of the INC.

Figure 19:
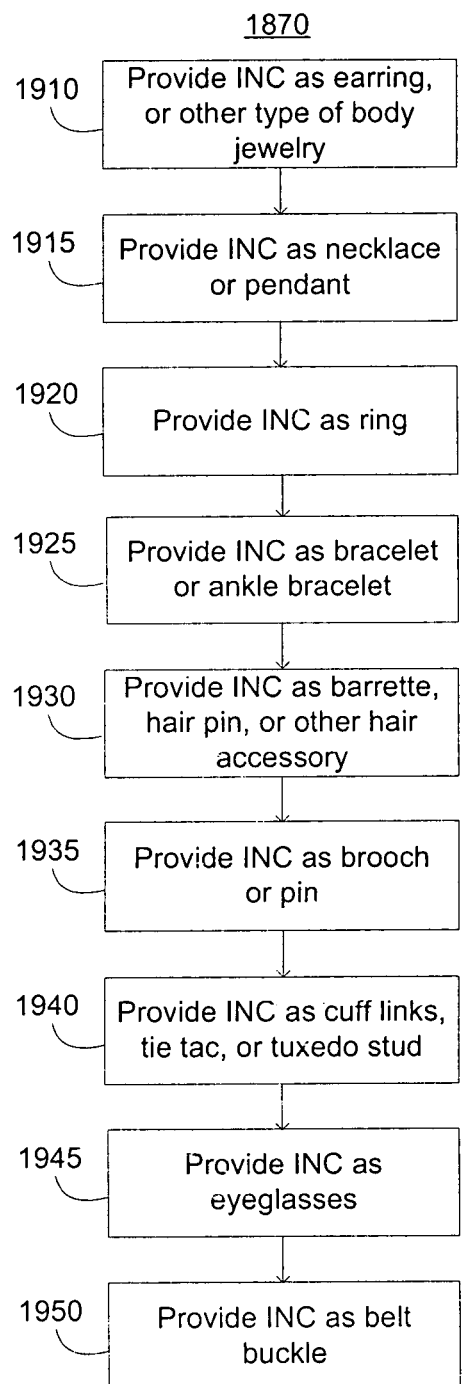
FIG. 19 is a flowchart of an illustrative process for allowing individual network components to be incorporated into items of jewelry.

Flowchart 1870 of FIG. 19 shows more detailed illustrative methods for designing INCs to be worn as items of jewelry. All steps in flowchart 1870 are optional and may be performed in any suitable order.

In step 1910, an INC may be configured as an earring, or other type of body jewelry designed to be worn in a pierced body part. A pair of earring INCs may perform complementary functions. One example of an earring INC may include a wireless receiver and a speaker. Two such INCs may function as a pair, providing stereo outputs. These INCs allow other INCs to send audio content to be played in close proximity to the user's ear, at a low and unobtrusive volume. Another example of an earring INC may include an antenna for a GPS receiver or a mobile telephone or other communications device. The received signal may be remodulated and sent to another INC for processing. These are merely examples, and any other suitable function may be performed by an earring INC. An INC may also be incorporated into an item of body jewelry designed to be worn in any other pierced body part, such as nose, tongue, nipple, etc.

In step 1915, an INC may be configured as a necklace or pendant. A pendant, for example, may be any appropriate INC, such as a control unit, a display device, a user input device, a GPS receiver, or any other suitable function or combination of functions. If the INC is configured as a necklace, the electronic components may be incorporated into a specific portion or segment of the necklace, or they may be distributed about the necklace.

In step 1920, an INC may be configured as a ring. Examples of suitable ring INCs may include a user input device, such as a push button or a microphone. Any other type of suitable device may be implemented as a ring INC, such as a digital camera, a pulse oximeter, a heart rate sensor, a blood pressure sensor, a simple display device, etc.

In step 1925, an INC may be configured as a bracelet or as an ankle bracelet, or as similar jewelry to be worn around any other part of the body. With this type of INC, the electronic components may be incorporated into a specific portion or segment of the band, or they may be distributed about the band.

In step 1930, an INC may be configured as a barrette, a hairpin, or any other type of hair accessory, such as a hair band. An antenna would be an example of a suitable function to incorporate into this type of INC. In step 1935, an INC may be configured as a pin or brooch. In step 1940, an INC may be configured as cuff links, a tie tack, a tuxedo stud, or other similar item. An INC with any suitable function may be attached to the clothing in such a manner, such as a communication device, a user input device, etc.

In step 1945, an INC may be incorporated into a pair of eyeglasses. For example, the temple of the eyeglasses may incorporate an antenna or a speaker. In step 1950, an INC may be configured as a belt buckle. For example, such an INC may include a user input device.

These steps are merely illustrative of the types of INC jewelry that may be created. An INC may be configured as any type of jewelry, and may incorporate any suitable function. The function chosen for a particular INC may be based on the size of the item of jewelry and on the location on the body on which it is worn.

Figure 20:
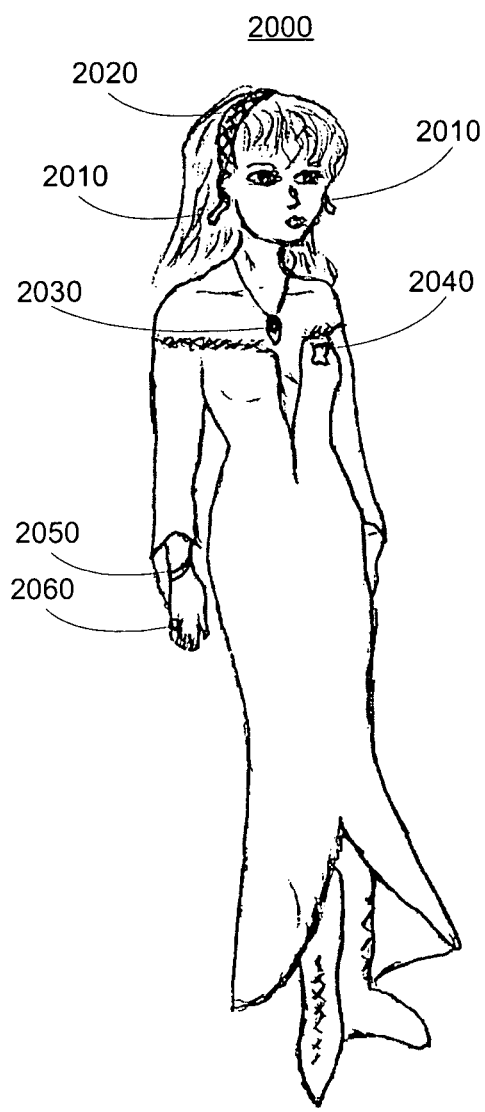
FIG. 20 shows an example of an MPN including several INCs incorporated into items of jewelry.

FIG. 20 shows an illustrative user with a jewelry-based MPN 2000. INCs 2010 are earring-based INCs, and may incorporate speakers. INC 2020 is a hair band INC, and may incorporate a mobile telephone antenna. INC 2030 is a pendant-based INC, and may incorporate a microphone. INC 2040 is a brooch INC, and may incorporate a processor and memory, and may operate as a control unit. INC 2050 is a bracelet INC, and may include a user input device (such as a numeric key input). INC 2060 is a ring-based INC, and may include a separate user input device. As an example, MPN 2000 may provide a mobile communication system to the user, along with other functions. The types of jewelry and the functions provided are merely illustrative. Any suitable INCs can be provided and they may provide any suitable combination of functions. If desired, an MPN that incorporates jewelry-based INCs can also incorporate other types of INCs that are not jewelry-based.

A single item of jewelry can include multiple modules, which can be individually added, removed, or replaced. A charm bracelet allows the user to add multiple charms. A modular bracelet may allow the user to add or replace individual links. Similarly, a modular necklace or ankle bracelet may allow the user to add and replace individual links.

Each link or charm may act as a separate INC in an MPN. A single jewelry item can contain many INCs, each of which may provide a different function. If desired, multiple modules may provide similar functions, such as memory. As an example, one link in a modular bracelet may act as a control unit, several may provide additional memory, one may provide an input sensor (e.g., a temperature sensor or a heart rate sensor), and one may provide a user input device.

If desired, the entire item of jewelry may act as a single INC. For example, one of the modules may provide the wireless transceiver used by all of the other modules to communicate within the MPN. Alternatively, the base jewelry item (e.g., the modular bracelet without any added links) may provide basic INC functionality. For example, the bracelet may include a wireless transceiver, a PC connection, a processor and other control circuitry, memory, power, and security-processing circuitry. Each added jewelry module may include only the electronic necessary to add a specific function, along with any desired aesthetic features. The base jewelry system may act as a communication and power bus for transferring data and power among the jewelry modules in the system.

Figure 21:
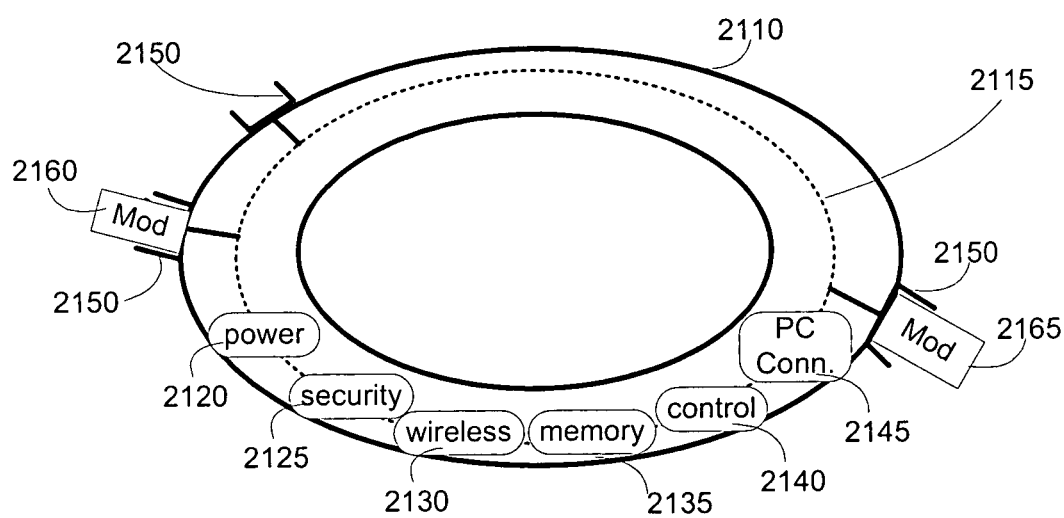
FIG. 21 is a block diagram of a modular jewelry system.

FIG. 21 shows a block diagram of illustrative modular jewelry system 2100. Bracelet 2110 provides the base unit to which the jewelry modules are added. It includes power and communication bus 2115, which may be used to carry power to each of the internal subsystems (2125, 2130, 2135, 2140, and 2145) in the bracelet as well as to the added modules (e.g., modules 2160 and 2165). Bus 2115 also carries data among the internal subsystems and added modules.

Power subsystem 2120 provides power to the bracelet, both the internal subsystems and any added modules. It may be similar to power module 660 shown in FIG. 7. Security-processing subsystem 2125 provides security features for the modules added to the system. In addition, each module may include its own security-processing subsystem. Security-processing subsystem 2125 may be similar to security-processing circuitry 543 discussed in conjunction with FIG. 5. Wireless transceiver 2130 provides wireless communication between the bracelet (any of its internal subsystems or added modules) and any external INCs. Memory 2135 provides storage of any appropriate type (e.g., RAM, ROM, or flash memory). It may be used by the internal subsystems as well as by any of the added modules. Control subsystem 2140 may include a processor. It may also include any other circuitry suitable for controlling the internal subsystems, for controlling the added modules, for coordinating data sent between and among subsystems and modules, and any other suitable function. PC connection subsystem 2145 may provide hardware and software to interface the modular jewelry system with a personal computer. It may be similar to PC connection 620 described in conjunction with FIG. 6.

Modular jewelry system 2100 may include multiple module connections 2150. Each connection 2150 provides the physical attachment means for attaching a module to the base unit. Each connection 2150 also provides the electrical connection between the added module and power and communication bus 2115. Preferably, connection 2150 is designed to a standard physical and electrical specification, which is published to manufacturers of individual modules. Each module is preferably manufactured to the same specification, so that any module is interchangeable with any connection on any base system. In addition, the standard specification may detail a communications protocol by which individual modules may make their capabilities available and may take advantage of the capabilities of other subsystems and modules. Modules 2160 and 2165 are examples of jewelry modules added to modular jewelry system 2100. They may provide any suitable functions or combination of functions. Each module may include its own aesthetic design, or the modules may share a common design.

If desired, bracelet 2110 may include any suitable additional functions as internal subsystems, so that they do not need to be added as modules. The internal subsystems shown are merely illustrative and may vary. Although a modular bracelet is shown in this example, any other suitable type of modular jewelry may be used in this system, such as a charm bracelet, a modular necklace, a modular ankle bracelet, or a modular belt.

If desired, modular jewelry system 2100 may function as a standalone unit and network, rather than functioning as a component in a modular personal network. In this case, wireless transceiver 2130 need not be included. In this type of network, functions are added, removed, or changed by adding, removing, or replacing individual jewelry modules. In addition, functions of the modular jewelry system may be changed by downloading different software using PC connection 2145. Software can be downloaded into an internal subsystem (such as memory 2135) or into an added module, such as module 2160.

Figure 22:
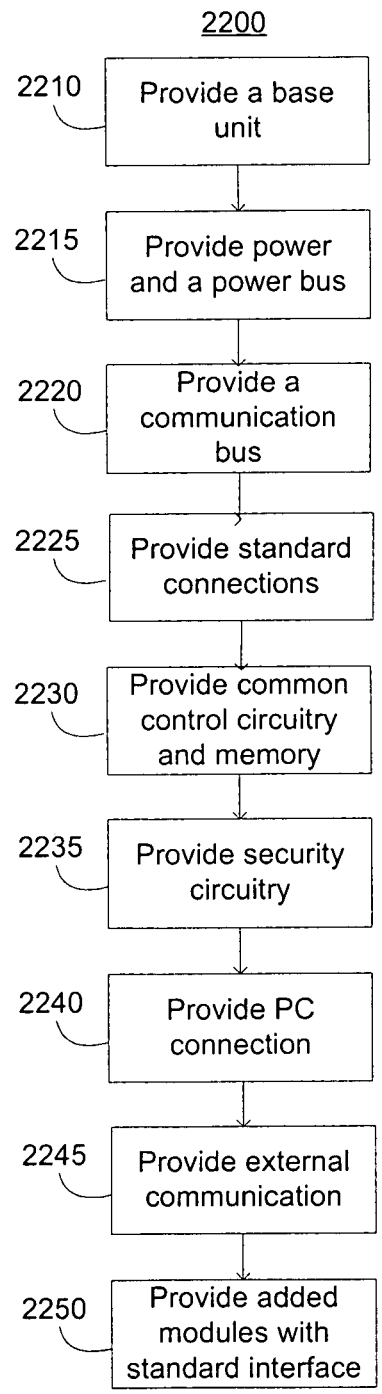
FIG. 22 is a flowchart of an illustrative process for providing a modular jewelry system.

FIG. 22 shows flowchart 2200 of an illustrative process for providing a modular jewelry system. All steps are optional and may be performed in any suitable order. In step 2210, a base unit may be provided. The base unit may be, for example, a modular bracelet, a charm bracelet, a modular necklace, a modular ankle bracelet, a modular belt, or any other suitable type of unit. In step 2215, the base unit may include power and a power bus for distributing the power among internal and external components. In step 2220, the base unit may include communication bus for distributing data among internal and external components. In step 2225, the base unit may include multiple standard connections for attaching jewelry modules. Each connection may be manufactured to a standard specification to provide a physical connection to the base unit, an electrical connection to the power bus, and an electrical connection to the communication bus. In step 2230, the base unit may include common control circuitry. This may include a processor, memory of any suitable type, and any other circuitry for supporting the internal and external components. In step 2235, the base unit may include security circuitry. This circuitry may interface with security circuitry in added modules to ensure that, once a module has been identified as belonging to a specific system, it cannot be moved to another modular jewelry system without user authorization. It may also function to ensure that the base unit itself cannot be used in a different MPN once it has been configured by a particular user. In step 2240, a PC connection may be provided. This may allow information to be sent from a personal computer to the base unit or any attached modules, as well as allowing information to be sent from the base unit and any modules to a personal computer. This may include software, data, configuration information, or any other suitable information. In step 2245, external communication may be provided by the base unit. This may include, for example, a wireless transceiver as well as suitable software and hardware protocols. In step 2250, a variety of modules may be provided to be added to the modular jewelry system. Each may conform to the physical, electrical, and protocol specifications published to manufacturers of such modules. Each module may provide one or more suitable functions to the system. Each may include its own security circuitry to ensure that it cannot be misused once it has been configured for a specific user and modular jewelry system.

A circuit or circuitry for implementing different techniques or functionality illustratively described herein may comprise hardware (e.g., discrete electronic circuit components), software, or a combination thereof configured to provide such techniques or functions.

Thus, we have provided systems and methods for improvements to a modular personal network. One skilled in the art will appreciate that the present invention can be practiced by other than the described embodiments, which are presented for the purposes of illustration and not of limitation. Other embodiments are possible, including other uses, functions, components, and combinations thereof. The present invention is limited only be the claims that follow.

We claim:

1. A modular personal network system comprising:
    a plurality of jewelry individual network components that are configured to wirelessly communicate with each other using a wireless network protocol;
    wherein each jewelry individual network component is configured to be worn or carried by a user;
    wherein each jewelry individual network component is configured to store that component's device identification information and to transmit the device identification information to other individual network components using the wireless network protocol;
    wherein each jewelry individual network component is configured to store network identification information that identifies the modular personal network in which the individual network components are operating; and
    wherein each jewelry individual network component is configured such that, prior to reducing its power consumption and being removed from the modular personal network, it is capable of transmitting status information to the remaining individual network components using the wireless network protocol in response to a determination that the user desires to reduce its power consumption and remove it from the modular personal network.

2. The system of claim 1, wherein at least one of the jewelry individual network components is an earring, the earring comprising:
    a mount configured to be worn in the user's pierced ear;
    a wireless receiver for receiving audio information; and
    a speaker for playing the audio information.

3. The system of claim 1, wherein at least one of the jewelry individual network components is an earring, the earring comprising:
    a mount configured to be worn in the user's pierced ear;
    an antenna for receiving radio frequency signals;
    a demodulator for processing the received signals;
    a modulator for converting the processed signals; and
    a wireless transmitter for sending the converted signals to another one of the jewelry individual network components worn by the user.

4. The system of claim 1, wherein at least one of the jewelry individual network components is a ring, the ring comprising:
    a mount configured to be worn around the user's finger;
    a wireless transceiver configured to communicate with another one of the jewelry individual network components worn by the user; and
    a display screen.

5. The system of claim 1, wherein at least one of the jewelry individual network components is configured to enable a new function for the user that is not provided by any other one of the jewelry individual network components in the modular personal network.

6. The system of claim 1, wherein at least one of the jewelry individual network components is configured to automatically join the modular personal network.

7. The system of claim 1, wherein the modular personal network is configured to continue to operate with any remaining individual network components even after one of the individual network components is removed.

8. The system of claim 1, wherein the status information comprises the device identification information for the individual network component that is transmitting the status information.

9. The system of claim 1, wherein the status information comprises an instruction for the remaining individual network components to change their level of power consumption.

10. The system of claim 9, wherein the instruction for the remaining individual network components to change their level of power consumption comprises a command for the remaining individual network components to enter a low power consumption state.

11. The system of claim 1, wherein the remaining individual network components are configured to change their levels of power consumption in response to the receipt of the status information.

12. A modular personal network system comprising:
a first individual network component configured to be worn or carried by a user; and
a second individual network component configured to be worn or carried by the user,
wherein the first and second individual network components are configured to wirelessly communicate with each other over a modular personal network,
wherein the first individual network component is configured to determine that the user desires to reduce the power consumption of the first individual network component and for the first individual network component to be removed from the modular personal network, and
wherein the first individual network component is configured to communicate information about its status to the second individual network component in response to the determination that the user desires to reduce the power consumption of the first individual network component and for the first individual network component to be removed from the modular personal network, wherein the communication of the information about the status of the first individual network occurs prior to the first individual network component reducing its power consumption and being removed from the modular personal network.

13. The system of claim 12, wherein the information about the status of the first individual network component comprises device identification information for the first individual network component.

14. The system of claim 12, wherein the information about the status of the first individual network component comprises an indication that the first individual network component will be reducing its power consumption.

15. The system of claim 12, wherein the information about the status of the first individual network component comprises an indication that the first individual network component will be powering off.

16. The system of claim 12, wherein the second individual network component is configured to reduce its power consumption in response to receiving the information about the status of the first individual network component.

17. The system of claim 12, wherein the second individual network component is configured to communicate information about its status to the first individual network component after receiving the information about the status of the first individual network component.

18. The system of claim 17, wherein the first individual network component is configured to increase its power consumption in response receiving the communication about the status of the second individual network component.

19. A method for execution by a first individual network component of a modular personal network that is configured to be worn or carried by a user, the method comprising:
the first individual network component receiving a user input;
in response to the user input, the first individual network component determining that the user desires to reduce the power consumption of the first individual network component and for the first individual network component to be removed from the modular personal network;
in response to the determination that the user desires to reduce the power consumption of the first individual network component and for the first individual network component to be removed from the modular personal network, the first individual network component communicating information about its status to a second individual network component, which is also configured to be worn or carried by the user; and
the first individual network component reducing its power consumption and being removed from the modular personal network after communicating the information about its status to a second individual network component.

20. The method of claim 19, wherein the information about the status of the first individual network component comprises device identification information for the first individual network component.

21. The method of claim 19, wherein the information about the status of the first individual network component comprises an indication that the first individual network component will be reducing its power consumption.

22. The method of claim 19, wherein the information about the status of the first individual network component comprises an indication that the first individual network component will be powering off.

23. The method of claim 19, further comprising the first individual network component receiving a communication about the status of the second individual network component.

24. The method of claim 19, further comprising, in response to the first individual network component receiving a communication about the status of the second individual network component, the first individual network component increasing its power consumption.

* * * * *